(12) United States Patent
Yayon et al.

(10) Patent No.: US 7,714,107 B2
(45) Date of Patent: *May 11, 2010

(54) FREEZE-DRIED FIBRIN MATRICES AND METHODS FOR PREPARATION THEREOF

(75) Inventors: Avner Yayon, Moshav Sitria (IL); Malkit Azachi, Rehovot (IL); Micha Gladnikoff, Tel Aviv (IL)

(73) Assignee: ProChon Biotech Ltd., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,387

(22) Filed: Jul. 26, 2005

(65) Prior Publication Data

US 2006/0172008 A1 Aug. 3, 2006

Related U.S. Application Data

(63) Continuation of application No. PCT/IL2004/000088, filed on Jan. 29, 2004.

(60) Provisional application No. 60/507,167, filed on Oct. 1, 2003.

(30) Foreign Application Priority Data

Jan. 30, 2003 (IL) .................... 154208

(51) Int. Cl.
*A61K 35/14* (2006.01)
(52) U.S. Cl. ............ 530/381; 530/350; 435/343; 424/422; 424/93.7; 424/400
(58) Field of Classification Search .......... None
See application file for complete search history.

(56) References Cited

U.S. PATENT DOCUMENTS

| 4,442,655 | A | 4/1984 | Stroetmann | 53/428 |
|---|---|---|---|---|
| 4,642,120 | A | 2/1987 | Nevo et al. | 623/16 |
| 5,206,023 | A | 4/1993 | Hunziker | 424/423 |
| 5,260,420 | A | 11/1993 | Burnouf-Radosevich et al. | 530/382 |
| 5,368,858 | A | 11/1994 | Hunziker | 424/423 |
| 5,411,885 | A | 5/1995 | Marx | 435/240.2 |
| 5,443,950 | A | 8/1995 | Naughton et al. | 435/1 |
| 5,466,462 | A | 11/1995 | Rosenthal et al. | 424/426 |
| 5,631,011 | A * | 5/1997 | Wadstrom | 424/400 |
| 5,700,476 | A | 12/1997 | Rosenthal et al. | 424/426 |
| 5,842,477 | A | 12/1998 | Naughton et al. | 128/898 |
| 5,972,385 | A | 10/1999 | Liu et al. | 424/486 |
| 6,293,970 | B1 * | 9/2001 | Wolfinbarger et al. | 623/23.61 |
| 6,310,267 | B1 | 10/2001 | Rapp | 602/41 |
| 6,440,427 | B1 | 8/2002 | Wadstrom | 424/400 |
| 6,486,377 | B2 | 11/2002 | Rapp | 602/41 |
| 6,548,729 | B1 * | 4/2003 | Seelich et al. | 602/48 |
| 7,335,508 | B2 * | 2/2008 | Yayon et al. | 435/343 |

FOREIGN PATENT DOCUMENTS

| WO | WO 99/15209 | 4/1999 |
|---|---|---|
| WO | WO 03/007873 A2 | 1/2003 |

OTHER PUBLICATIONS

Wells, Biochemistry, vol. 29, pp. 8509-8517, 1990.*

* cited by examiner

*Primary Examiner*—Hope A Robinson
(74) *Attorney, Agent, or Firm*—Winston & Strawn LLP

(57) ABSTRACT

The present invention relates to porous freeze-dried fibrin matrices substantially devoid of external anti-fibrinolytic agents, and methods of producing such matrices. Resilient matrices, also known as sponges, that are particularly beneficial for supporting three dimensional cell growth are obtained from plasma proteins substantially devoid of plasminogen or from partially purified plasma proteins, thus obviating the need for exogenous anti-fibrinolytic agents. Furthermore, incorporation of glycosaminoglycans and bioactive agents during the formation of the matrix results in a sponge having advantageous biological, mechanical and physical properties. The compositions of the present invention are useful clinically, without cells or as a cell bearing implants.

16 Claims, 13 Drawing Sheets

3 Days post seeding 3 days post seeding

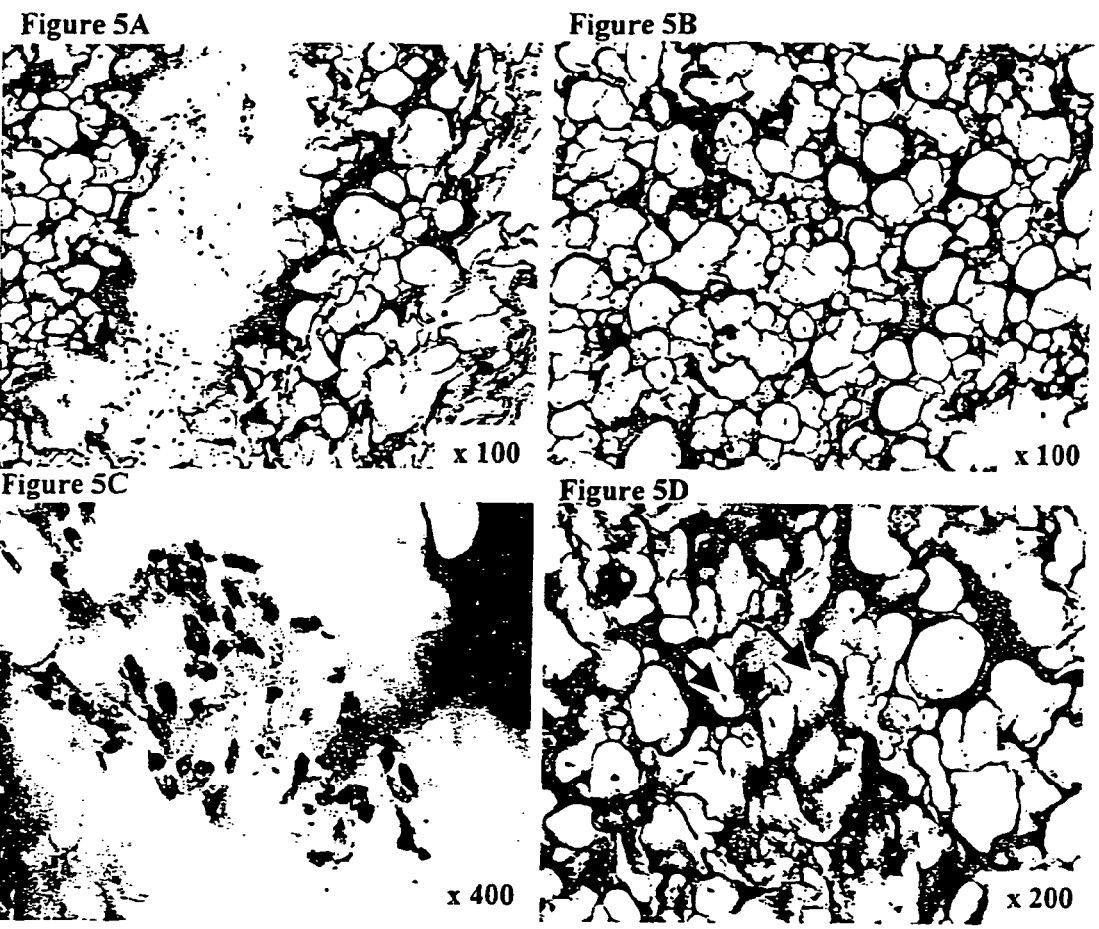

x400 Tol Blue + Fast red

X200 H&E

X400 H&E

FREEZE-DRIED FIBRIN MATRICES AND METHODS FOR PREPARATION THEREOF

CROSS-REFERENCE TO RELATED APPLICATIONS

This application is a continuation of International application PCT/IL2004/000088 filed Jan. 29, 2004, and claims the benefit of provisional application 60/507,167filed Oct. 1, 2003, the entire content of each of which is expressly incorporated herein by reference thereto.

FIELD OF THE INVENTION

The present invention concerns freeze-dried biomatrices comprising plasma proteins substantially devoid of plasminogen useful for clinical applications including as implants for tissue engineering. Additional preferred embodiments of the invention are freeze-dried plasma protein biomatrices substantially devoid of exogenous anti-fibrinolytic agents. The matrices according to the present invention are useful clinically, per se or as cell-bearing implants.

BACKGROUND OF THE INVENTION

Tissue Engineering. Tissue engineering may be defined as the art of reconstructing or regenerating mammalian tissues, both structurally and functionally (Hunziker, Osteoarth. Cart. 10: 432-63,2002). Tissue engineering generally includes the delivery of a synthetic or natural scaffold that serves as an architectural support onto which cells may attach, proliferate, and synthesize new tissue to repair a wound or defect.

An example of a tissue that is prone to damage by disease and trauma is the articular cartilage, one of several types of cartilage in the body, found at the articular surfaces of bones. Damage to cartilage may result from an inflammatory disease such as rheumatoid arthritis, from a degenerative process such as osteoarthritis or from trauma such as intraarticular fracture or following ligament injuries. Cartilage lesions are often associated with pain and reduced function, generally do not heal and without medical intervention may require total joint replacement.

Current therapeutic strategies for repairing damaged cartilage encompass procedures that induce a spontaneous repair response and those which reconstruct the tissue in a structural and functional manner. The former includes surgical techniques that expose the subchondral bone thereby allowing the infiltration of bone marrow progenitor cells to initiate the healing response. Often the induced tissue is of a mixed fibrocartilage type, is not durable and the clinical improvements are short lived. The latter strategy includes transplantation of chondral or osteochondral cells or tissue from either an autologous or an allogeneic source. Autologous Chondrocyte Transplantation (ACT) relies on transplanting into a cartilage lesion autologous chondrocytes, which have been isolated from a patient's cartilage biopsy and expanded in vitro. In fact, this technique requires a complicated procedure involving two surgical sites, and shows high variability and limited clinical success.

Matrices useful for tissue regeneration and/or as biocompatible surfaces useful for tissue culture are well known in the art. These matrices may therefore be considered as substrates for cell growth either in vitro or in vivo. Suitable matrices for tissue growth and/or regeneration include both biodegradable and biostable entities. Among the many candidates that may serve as useful matrices claimed to support tissue growth or regeneration are gels, foams, sheets, and porous structures of different forms and shapes.

Porous materials formed from synthetic and/or naturally occurring biodegradable materials have been used in the past as wound dressings or implants. A porous material provides structural support and a framework for cellular in-growth and tissue regeneration. Preferably, the porous material gradually degrades and is absorbed as the tissue regenerates. Typical bioabsorbable materials for use in the fabrication of porous wound dressings or implants include both synthetic polymers and biopolymers such as structural proteins and polysaccharides. The biopolymers may be either selected or manipulated in ways that affect their physico-chemical properties to provide greater or lesser degrees of flexibility or susceptibility to degradation.

Many natural polymers have been disclosed to be useful for tissue engineering or culture, including various constituents of the extracellular matrix including fibronectin, various types of collagen, and laminin, as well as keratin, fibrin and fibrinogen, hyaluronic acid, heparan sulfate, chondroitin sulfate and others. U.S. Pat. Nos. 6,425,918 and 6,334,968 disclose a freeze-dried bioresorbable polysaccharide sponge and use thereof as a matrix or scaffold for implantation into a patient.

Fibrin. Fibrinogen is a major plasma protein, which participates in the blood coagulation process. Upon blood vessel injury, fibrinogen is converted to insoluble fibrin which serves as the scaffold for a clot. Blood coagulation of is a complex process comprising the sequential interaction of a number of plasma proteins, in particular of fibrinogen (factor 1), prothrombin (factor II), factor V and factors VII-XIII. Other plasma proteins such as Von Willebrand factor, immunoglobulins, coagulation factors and complement components also play a part in the formation of blood clots.

Fibrin is known in the art as a tissue adhesive medical device useful for wound healing and tissue repair. Lyophilized plasma-derived protein concentrate (comprising fibrinogen, Factor XIII and fibronectin), in the presence of thrombin and calcium ions forms an injectable biological sealant (fibrin glue). U.S. Pat. No. 5,411,885 discloses a method of embedding and culturing tissue employing fibrin glue.

U.S. Pat. No. 4,642,120 discloses the use of fibrinogen-containing glue in combination with autologous mesenchymal or chondrocytic cells to promote repair of cartilage and bone defects. U.S. Pat. No. 5,260,420 discloses a method for preparation and use of biological glue comprising plasma proteins for therapeutic use. U.S. Pat. No. 6,440,427 provides an adhesive composition consisting substantially of fibrin forming components and a viscosity enhancing polysaccharide such as hyaluronic acid. A freeze-dried fibrin clot for the slow release of an antibiotic is described by Itokazu (Itokazu et al., Infection 25:359-63, 1997).

U.S. Pat. No. 5,972,385 discloses a lyophilized crosslinked collagen-polysaccharide matrix, with optional fibrin, that is administered per se or in combination with therapeutics for tissue repair. U.S. Pat. Nos. 5,206,023 and 5,368,858 disclose a method and composition for inducing cartilage repair comprising dressing the site with a biodegradable matrix formed by mixing matrix forming material with a proliferative agent and a transforming factor.

A fibrinogen-containing freeze-dried fleece-like structure for use as a wound dressing, filling for bone cavities or support material for release of active materials has been disclosed in U.S. Pat. No. 4,442,655. The structure is prepared by premixing fibrinogen and thrombin solutions, pouring into a mold, freezing and lyophilizing.

A freeze-dried fibrin web for wound healing has been disclosed in U.S. Pat. Nos. 6,310,267 and 6,486,377. The preparation of said web necessitates a single- or multi-stage dialysis of the fibrinogen solution. According to that disclosure, the single-stage or multistage dialysis of the fibrinogen solution changes crucially its composition by reducing the concentration of salts and amino acids. The dialysis is carried out in an aqueous solution of a physiologically compatible inorganic salt and an organic complexing agent.

A storage stable fibrin sponge containing a blood clotting activator for hemostasis, tissue adhesion, wound healing and cell culture support is disclosed in WO 99/15209. According to that disclosure, the restoration of moisture or water content following lyophilization is crucial for obtaining a soft, adaptable, absorbent sponge. The sponge may be impregnated with additives such as a blood clotting activator, stabilizers, preservatives and other agents.

U.S. Pat. Nos. 5,466,462 and 5,700,476 disclose a bioresorbable heteromorphic sponge comprising a biopolymer matrix structure, at least one substructure and at least one pharmacologically active agent. The substructures allow the incorporation of one or more active agents into the final product for physic release. U.S. Pat. No. 5,443,950 relates to the growth of cells derived from a desired tissue on a pre-established stromal support matrix. U.S. Pat. No. 5,842,477 discloses a method of in vivo cartilage repair by implanting a biocompatible, three-dimensional scaffold in combination with periosteal/perichondrial tissue and stromal cells, with or without bioactive agents.

Fibrinolysis

Existing freeze-dried fibrin implants for tissue engineering purposes are prepared using fibrinogen or plasma protein solutions having inherent proteases that may compromise the stability of certain of the plasma proteins and lead to degradation of the matrix. Plasminogen is a major plasma protein that binds fibrin during clot formation. Within the clot or matrix, plasminogen is enzymatically converted to plasmin, which functions as a fibrinolytic agent, resulting in the degradation of the clot or matrix. This process is typically retarded by the addition of anti-fibrinolytic agents, including but not limited to aprotinin, $\epsilon$-aminocaproic acid or tranexamic acid into the composition. These agents may have detrimental effects on cell growth, proliferation and/or differentiation or may cause adverse reactions in patients. The art has not heretofore provided a stable freeze-dried fibrin matrix substantially devoid of exogenous anti-fibrinolytic agents.

Copending international patent application WO 03/007873 by some of the applicants of the present invention of the present invention, discloses a freeze-dried plasma protein matrix comprising plasma proteins and at least one anti-fibrinolytic agent, optionally comprising selected auxiliary agents to improve certain physical, mechanical and biological properties of the matrix.

Thus, there remains an unmet need for a fully biocompatible, true three-dimensional, plasma protein matrix, for in vitro and in vivo cell growth and tissue regeneration, substantially devoid of fibrinolytic activity and exogenous anti-fibrinolytic agents thus obviating the need for exogenous anti-fibrinolytic agents.

SUMMARY OF THE INVENTION

The present invention relates to biomatrices substantially devoid of external anti-fibrinolytic agents, which have been shown to be deleterious to cells and tissue and which may induce adverse reactions in patients. It is now disclosed for the first time that resilient, non-brittle, matrices, also known as sponges, that are particularly beneficial for supporting three dimensional cell growth may be obtained from plasma proteins substantially devoid of plasminogen, thus obviating the need for external anti-fibrinolytic agents. It is further disclosed that unexpectedly biomatrices obtained from partially purified plasma proteins also obviates the need for exogenous anti-fibrinolytic agents. The compositions and methods of the present invention are effective for in vivo and in vitro applications including as biocompatible implants for tissue engineering as well as in biotechnology for the in vitro culturing and differentiation of cells. The matrices according to the present invention are three-dimensional (3D) and may be used clinically, per se or as cell-bearing implants. The present invention provides all components fundamental for tissue repair, thus facilitating the medical practitioner's task and providing a superior alternative for tissue reparation and regeneration in a patient.

The present invention provides a porous, freeze-dried fibrin matrix formed from plasma proteins comprising fibrinogen, thrombin and Factor XIII, the matrix having less than 10% residual moisture and being substantially devoid of exogenous anti-fibrinolytic agents and of organic chelating agents, which exhibits superior characteristics. The present invention is based in part on the unexpected finding that a matrix comprising plasma proteins substantially devoid of exogenous anti-fibrinolytic agents and plasminogen imparts superior stability and significantly improves cell seeding and cell dispersion while retaining other positive attributes of these matrices. The plasminogen-free matrices in particular exhibit reduced resorbability compared to fibrin matrices known in the art, providing a long lasting implant with enhanced stability and endurance for successful tissue growth, repair and regeneration.

In one aspect, the present invention relates to a porous freeze-dried fibrin matrix formed from plasma proteins substantially devoid of exogenous anti-fibrinolytic agents and of organic chelating agents. According to one embodiment the plasma proteins are purified from a plasma source or may be used from a commercially available source, including native or recombinant proteins, in the substantial absence of exogenous anti-fibrinolytic agents and of organic chelating agents. According to another embodiment the plasma protein source is selected from total blood, blood fractions, blood derivative, cryoprecipitate, recombinant proteins, plasma and plasma fractions. The plasma proteins may be selected from xenogeneic, allogeneic and autologous plasma sources. According to one embodiment the plasma source is autologous.

In another aspect, the present invention provides a porous freeze-dried fibrin matrix formed from plasma proteins comprising fibrinogen, thrombin and Factor XIII, the matrix having less than 10% residual moisture and being substantially devoid of exogenous anti-fibrinolytic agents, plasminogen and of organic chelating agents. In one embodiment substantially devoid of plasminogen refers to the plasma protein solution comprising less than about 20% of plasminogen normally present in blood plasma, preferably less than about 10% of the plasminogen normally present in plasma and more preferably less than about 5% of the plasminogen normally present in plasma. The inventors have discovered that a porous freeze-dried fibrin matrix comprising plasma proteins substantially devoid of plasminogen provides a superior matrix for clinical and biotechnological applications. In addition to eliminating the need for exogenous anti-fibrinolytic agents and their concomitant detrimental effects, the inventors now show that the fibrin matrix of the present invention is superior as a scaffold for cell seeding, growth and differentiation and for use in tissue repair and regeneration.

The fibrin matrix of the invention may be used per se, comprising plasma proteins substantially devoid of exogenous anti-fibrinolytic agents and of organic chelating agents, for clinical and biotechnological applications. It may however, further comprise additives that impart additional advantageous biological, physical and mechanical characteristics to the matrix. The present invention encompasses the incorporation into the matrix of at least one additive to provide a matrix having improved biological, mechanical and/or physical properties.

Copending international patent application WO 03/007873 by some of the applicants of the present invention discloses a fibrin matrix comprising plasma proteins and at least one anti-fibrinolytic agent, optionally further comprising agents such as polysaccharides, anionic polysaccharides, glycosaminoglycans, or synthetic polymers added in the preparation to improve certain physical, mechanical and biological properties of the matrix. The requirement for an anti-fibrinolytic agent has now been removed or overcome by the substantial absence of plasminogen in the matrix.

In one embodiment, the present invention is related to a porous fibrin matrix substantially devoid of exogenous anti-fibrinolytic agents, plasminogen and of organic chelating agents further comprising at least one additive selected from the group consisting of polysaccharides, glycosaminoglycans (GAGs) and synthetic polymers that is useful as a support for growth and differentiation of cells, both in vitro and in vivo.

According to one embodiment the additive may be added ab initio, i.e., during formation of the clot. According to alternative embodiments the additive is introduced to the matrix any time following formation of the matrix. According to various embodiments of the present invention, the matrix is prepared using at least one glycosaminoglycan selected from the group consisting of crosslinked hyaluronic acid, non-crosslinked hyaluronic acid, heparin and heparin derivatives and heparin mimetics, chondroitin sulfate, dextran sulfate, dermatan sulfate, heparan sulfate and keratan sulfate.

The glycosaminoglycan is added to the matrix at a final concentration that imparts suppleness and elasticity to the matrix and precludes the need for adjusting the moisture content of the final composition. According to one embodiment of the present invention the glycosaminoglycan is selected from crosslinked and non-crosslinked hyaluronic acid. In one embodiment the concentration of non-crosslinked hyaluronic acid is about 0.005% to about 0.5% final (V/V) more preferably about 0.05% to about 0.1%. In another embodiment the concentration of crosslinked hyaluronic acid is about 0.001% to about 0.1% and more preferably about 0.05% to about 0.09% final (V/V). According to another embodiment the glycosaminoglycan is selected from heparin and heparin derivatives.

The present invention further encompasses a fibrin matrix comprising at least one bioactive agent selected from the group consisting of therapeutic proteins, platelets and platelet supernatant, analgesics, anti-microbial or anti-inflammatory agents and enzymes.

According to one embodiment the present invention provides a freeze-dried porous matrix comprising plasma proteins substantially devoid of exogenous anti-fibrinolytic agents, plasminogen and of organic chelating agents, further comprising at least one glycosaminoglycan and at least one bioactive agent.

According to another embodiment of the present invention the at least one bioactive agent is a therapeutic protein selected from the group consisting of growth factors and their variants. In one aspect, the growth factor is selected from a fibroblast growth factor (FGF) and variants thereof. In another aspect, the FGF is an FGF having the capacity to induce or enhance cartilage and bone repair and regeneration and or angiogenesis. The growth factors may be incorporated at a wide range of concentrations, depending on the potency of the factor and the intended application.

For certain applications, sustained or phasic release of a bioactive agent may be preferred. In one embodiment, the at least one growth factor is incorporated in to the fibrin matrix directly, ab initio. In another embodiment, the at least one growth factor is bound to a carrier molecule such as heparin and is incorporated into the matrix ab initio. Sustained release of a bioactive agent depends on several factors including growth factor concentration, type of glycosaminoglycan incorporated and fibrin and thrombin concentration.

In contrast to the bioabsorbable heteromorphic sponge of the art, the present inventors now disclose a freeze-dried fibrin sponge comprising plasma proteins substantially devoid of exogenous anti-fibrinolytic agents, plasminogen and of organic chelating agents optionally comprising at least one additive selected from the group consisting of polysaccharides, glycosaminoglycans and synthetic polymers and optionally further comprising at least one bioactive agent.

According to one embodiment, the present invention provides a porous freeze-dried fibrin matrix comprising plasma proteins substantially devoid of exogenous anti-fibrinolytic agents, plasminogen and of organic chelating agents, further comprising at least one glycosaminoglycan and at least one bioactive agent. According to another embodiment of the invention the at least one glycosaminoglycan is selected from heparin and derivatives thereof, the at least one bioactive agent is a therapeutic protein selected from the FGF family of growth factors and variants thereof. This sponge provides phasic release of the FGF from the matrix and may be beneficial in certain therapeutic applications.

According to another embodiment the present invention provides a porous freeze-dried fibrin matrix comprising plasma proteins substantially devoid of exogenous anti-fibrinolytic agents, plasminogen and of organic chelating agents further comprising hyaluronic acid, heparin and at least one bioactive agent. The hyaluronic acid is selected from crosslinked and non-crosslinked hyaluronic acid. Preferably, the hyaluronic acid and the heparin or heparin derivative are incorporated into the sponge ab initio. The bioactive agent such as a growth factor may be incorporated into the sponge per se or heparin bound. Preferably the growth factor is selected from the family of FGF therapeutic molecules.

Another aspect of the invention provides a method of preparing the porous fibrin matrix. A method for preparing a porous freeze-dried fibrin matrix having less than 10% residual moisture and being substantially devoid of exogenous anti-fibrinolytic agents and of organic chelating agents comprises the following steps:

providing a thrombin solution and a plasma protein solution wherein the plasma protein solution is substantially devoid of exogenous anti-fibrinolytic agents and of organic chelating agents;
  introducing the thrombin solution and the plasma protein solution to a solid receptacle or mold in the presence of calcium ions;
  incubating under conditions appropriate to achieve clotting;
  freezing the clotted mixture; and
  lyophilizing the clotted mixture, to obtain a sponge, and optionally seeding the sponge with cells prior to implantation.

According to one embodiment of the present invention the plasma proteins are partially purified plasma proteins.

According to another embodiment of the present invention the plasma proteins are devoid of plasminogen. According to yet another embodiment the plasma protein solution comprising less than about 20% of plasminogen normally present in blood plasma, preferably less than about 10% of the plasminogen normally present in plasma and more preferably less than about 5% of the plasminogen normally present in plasma.

According to one embodiment of the invention the porous fibrin sponge is prepared by transferring the thrombin solution into a mold or solid receptacle, adding the plasma protein solution to achieve clot formation; freezing the clotted mixture and lyophilizing. Alternatively, the plasma proteins are mixed with thrombin in the presence of calcium ions under conditions suitable for achieving clotting; the mixture is cast in a solid support prior to achieving clotting; the clotted mixture is frozen and lyophilized. It is to be understood that when incorporated, additives and bioactive agents are added independently of each other to either of the matrix forming solutions, i.e. the plasma proteins or the thrombin solution, prior to the formation of the clot or are placed into the mold or solid receptacle prior to, concurrently with or following addition of the thrombin.

In one embodiment the invention provides a heterogeneous porous fibrin matrix wherein particulate matter is incorporated into the sponge ab initio. Particulate matter may include materials such as calcium phosphate particles, bone chips or glass fibers that are able to impart certain advantageous properties to the matrix including strength, additional porosity or phasic release.

According to various embodiments of the present invention plasma proteins at a concentration of about 10 mg/ml to about 50 mg/ml, substantially devoid of anti-fibrinolytic agents, plasminogen and of organic chelating agents, are mixed with at least one glycosaminoglycan such as hyaluronic acid and/or heparin, the mixture is incubated and added to the thrombin solution in the solid support to achieve formation of a clot. The clot is subsequently frozen and lyophilized.

In one embodiment, prior to implantation or use with cells, the sponge is substantially dry and contains less than 15% residual moisture, preferably less than 10% residual moisture. Surprisingly, this property of the sponge has been shown to be particularly advantageous for cell seeding and attachment.

Another aspect of the present invention provides a method of treatment and use of the freeze-dried fibrin matrix substantially devoid of exogenous anti-fibrinolytic agents and of organic chelating agents for tissue regeneration and repair of injured, diseased or traumatized tissue, including cartilage and bone defects and other tissue types including but not limited to liver, pancreas, and cardiac tissue. The method of treatment described herein is advantageous in that it requires minimal preparation for use by the medical practitioner. Other advantageous properties derive from the absence of exogenous anti-fibrinolytic agent such as tranexamic acid and aprotinin, which may be detrimental to the patient and the tissue surrounding the implant. Additionally, the absence of an exogenous anti-fibrinolytic agent renders the sponge a superior scaffold for in vivo or in vitro cellular attachment, growth, proliferation, infiltration and differentiation.

According to one embodiment the sponge is implanted per se. In another embodiment the sponge is cut into at least one section of desired shape.

In one embodiment the sponge further comprises cells. According to another embodiment the cells are selected from stem cells or progenitor cells. According to yet another embodiment the cells are selected from chondrocytes, osteoblasts, hepatocytes, or mesenchymal, endothelial, epithelial, urothelial, endocrine, neuronal, pancreatic, renal and ocular cell types.

The in vivo uses of the porous fibrin matrix are manifold. The porous fibrin matrix may function as a scaffold for in vitro culturing of cells or as an implant per se, for providing mechanical support to a defective or injured site in situ and/or for providing a matrix within which cells from the defective or injured site invade, proliferate and/or differentiate. The matrix is useful in treating articular cartilage defects of any type, including chondral and subchondral defects, arising from trauma such as an accident or sports injury or disease such as osteoarthritis. The porous fibrin matrix may be used per se or in combination with other therapies. For example, for cartilage repair the porous fibrin matrix is useful in conjunction with other therapeutic procedures including chondral shaving, laser or abrasion chondroplasty, and drilling or microfracture techniques.

Other typical orthopedic applications include joint resurfacing, meniscus repair, non-union fracture repair, craniofacial reconstruction or repair of an invertebral disc. Furthermore, the porous fibrin matrix is useful as a coating on synthetic or other implants such as pins and plates, for example, in hip replacement procedures. Thus, the present invention further provides implants or medical devices coated with a finish comprising the porous fibrin matrix of the invention.

The porous fibrin matrix of the invention is useful, inter alia, as an unexpectedly advantageous support for cellular growth. The absence of exogenous anti-fibrinolytic agents results in a fibrin matrix that is fully compatible with in vitro and in vivo cell growth, proliferation and differentiation. An additional advantage of the fibrin matrix of the invention is its improved ability to absorb cells and maintain their viability. The need to hydrate or rinse the sponge of the invention prior to cell seeding is precluded by the absence of exogenous anti-fibrinolytic agents, thus rendering a sponge with superior cell incorporation capacity.

The porous fibrin matrix of the invention, being an effective scaffold supporting cell growth, may be utilized in vivo in reconstructive surgery, for example as a matrix for regenerating tissue comprising neuronal cells, hepatic cells, urothelial cells, osteoblasts, cardiovascular tissue and mammary tissue or any other cell types which it is desired to culture within a three dimensional support. Thus, the matrix of this invention may be used to construct living tissue equivalents, including but not limited to liver, pancreas, nerve, glands, tendons, skin, blood vessels, bone, tendon, ligaments, and other organ equivalents, among many others.

According to one embodiment of the present invention the matrix is a sponge or scaffold able to support the proliferation of a variety of cell types. In one aspect, the sponge is inoculated with cells and the cells are allowed to proliferate in vitro prior to in vivo implantation. Alternatively, the sponge is seeded with cells that have been cultured or harvested and the sponge comprising the cells is implanted in situ. In one embodiment the porous fibrin matrix useful as an implant for transplantation comprises autologous plasma proteins and autologous chondrocytes.

According to one embodiment the present invention provides a method of treating or repairing injured, diseased or traumatized tissue, the method comprising the step of implanting a porous freeze-dried fibrin matrix formed from plasma proteins comprising fibrinogen, thrombin and Factor XIII, the matrix having less than 10% residual moisture and being substantially devoid of exogenous anti-fibrinolytic agents and of organic chelating agents to the site of injury, disease or trauma. The tissue is selected from cartilage, bone, liver, mesenchymal, endothelial, epithelial, urothelial, endocrine, neuronal, pancreatic, renal and ocular tissue types. According to another embodiment the porous freeze-dried fibrin matrix formed from plasma proteins comprising fibrinogen, thrombin and Factor XIII, the matrix having less than 10% residual moisture and being substantially devoid of exogenous anti-fibrinolytic agents, plasminogen and of organic chelating agents is implanted into the site of injury disease or trauma.

Further provided is the use of an implant of the present invention for the treatment or repair of injured, diseased or traumatized tissue, the use comprising the step of implanting a matrix of the present invention to the site of injury, disease or trauma. The tissue is selected from cartilage, bone, liver, mesenchymal, endothelial, epithelial, urothelial, endocrine, neuronal, pancreatic, renal and ocular tissue types.

These and further embodiments will be apparent from the figures, detailed description and examples that follow.

BRIEF DESCRIPTION OF THE FIGURES

The present invention will be understood and appreciated more fully from the following detailed description taken in conjunction with the figures in which:

FIGS. 5A-5D show histochemical sections of a plasma protein comprising partially purified human plasma proteins seeded with porcine chondrocytes.

FIG. 8A shows the cell matrix formed after 1 week, as stained with toluidine blue and fast red. FIGS. 8B and 8C show histological sections of the neocartilage nodule stained with H&E, magnified ×200 and ×400, respectively.

DETAILED DESCRIPTION OF THE INVENTION

Figure 1A:
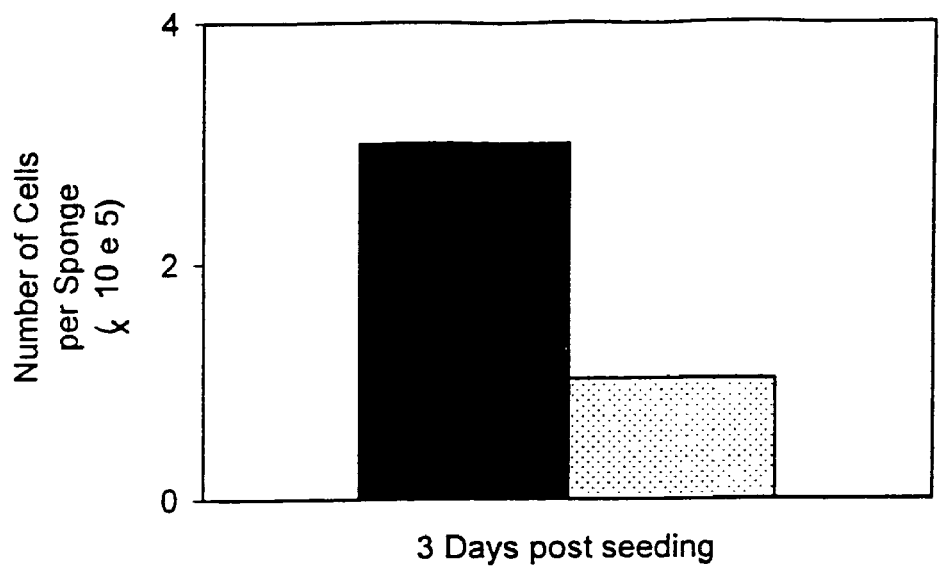
FIG. 1A shows a graph of porcine chondrocyte viability on the matrix substantially devoid of plasminogen compared to a standard sponge comprising an exogenous anti-fibrinolytic agent.

Though numerous biomatrices comprising plasma or tissue proteins are known in the art to which the present invention pertains, none has proven entirely satisfactory in meeting the criteria required for successful tissue engineering and tissue reparation. The present invention discloses a porous fibrin matrix, also referred to as a sponge, comprising plasma proteins substantially devoid of plasminogen and of organic chelating agents. The absence of plasminogen in the matrix obviates the need for external anti-fibrinolytic agents. It is further disclosed that unexpectedly biomatrices comprising partially purified plasma proteins also obviate the need for the addition of exogenous anti-fibrinolytic agents. The compositions and methods of the present invention are effective for in vitro and in vivo applications including as cell-bearing implants for tissue engineering and reparation.

The resulting fibrin, or plasma protein, sponge has attributes that make it particularly advantageous for supporting and promoting cell growth both in vivo and in vitro. Plasminogen is a plasma protein which is enzymatically converted to an active serine protease, plasmin, having fibrinolytic activity. This activity results in the rapid degradation of fibrin in fibrin glue and matrices. Anti-fibrinolytic agents such as tranexamic acid and aprotinin are typically incorporated into fibrin glue, sponges and matrices in order to maintain the integrity of the substrate. The sponges of the present invention are stable and exhibit reduced bioresorbability and overcome the need to add exogenous anti-fibrinolytic agents.

Among the advantageous properties of the matrices of the invention:

The fibrin matrices exhibit superior biological properties including reduced biodegradability, an absence of immunogenicity or other adverse reactions, the capacity to maintain and promote high levels of cell growth, proliferation, differentiation and migration and controlled release of bioactive agents.

The matrices have superior mechanical properties, controlled by varying the additives used in the composition. Desirable properties include suppleness, elasticity and durability.

The matrices have superior physical properties, which may be controlled by the additives used in the composition. The desirable properties include texture, pore size and interconnecting channels, hydrophilicity, hydrophilicity, adhesion, wettability, adherence and texture.

The plasma proteins can be retrieved from autologous or recombinant material thereby obviating the need for pooled blood sources with the attendant health risks.

The matrices of the invention provide all components fundamental for tissue repair, thus facilitating the medical practitioner's task. In addition, the composition of the sponge renders it suitable for minimally invasive surgery of articular cartilage. The sponge may be implanted in a mini-arthrotomy or arthroscopy procedure, thus avoiding the multiple site surgeries and a full arthrotomy used for ACT.

Definitions

For convenience and clarity certain terms employed in the specification, examples and claims are described herein.

"Plasma" as used herein refers to the fluid, non-cellular portion of the blood of humans or animals as found prior to coagulation.

"Plasma protein" as used herein refers to the soluble proteins found in the plasma of normal humans or animals. These include but are not limited to coagulation proteins, albumin, lipoproteins and complement proteins. The major plasma protein is fibrinogen, which upon cleavage by thrombin in the presence of calcium ions and Factor XIII, is converted to fibrin. A fibrin matrix may be used interchangeably with a plasma protein matrix.

As used herein the term "plasminogen" refers to plasminogen and plasmin. The terms "Substantially devoid of plasminogen" or "plasminogen-free" refer to plasma proteins having less than about 20% plasminogen normally present in plasma, preferably less than about 10% plasminogen normally present in plasma, preferably less than about 5% of the plasminogen normally present in plasma. Plasma normally compromises about 200 mg plasminogen per liter fresh plasma (about 2 µmol/liter). Plasminogen is the precursor to the active enzyme plasmin.

A "substantial absence of organic chelating agents" or "substantially devoid of organic chelating agents" refers to a concentration of less than 1 mm of an organic chelating agent such as EDTA or other organic chelating agents known in the art.

"Substantially devoid of exogenous anti-fibrinolytic agents" or "substantially devoid of external anti-fibrinolytic agents" refer to a plasma protein or fibrinogen solution to which no anti-fibrinolytic agents have been added. Non-limiting examples of antifibrinolytic agents include tranexamic acid (TEA), aprotinin and ε-aminocaproic acid (EACA). It is to be noted that small amounts of exogenous anti-fibrinolytic agents may be present in the plasma proteins due to processing methods.

"Platelet rich plasma" or "PRP" as used herein refers to plasma containing platelets. A platelet sample or platelet-derived extract or supernatant may be added exogenously. Alternatively, platelet rich plasma may be prepared by methods known in the art, including those disclosed in U.S. Pat. No. 6,475,175 and U.S. Pat. No. 6,398,972.

A "matrix" as used herein, refers to a porous structure, solid or semi-solid biodegradable substance having pores and interconnecting channels sufficiently large to allow cells to populate, or invade the matrix. The fibrin matrix of the invention may have irregular pores or substantially regular pores. As used herein, the term "substantially regular pores" means that the majority of the pores or more preferably substantially all the pores are in the same size range. The matrix-forming materials require addition of a polymerizing agent to form the matrix, such as addition of thrombin in the presence of bivalent calcium ions to a solution comprising fibrinogen to form a fibrin clot. The clot is subsequently freeze-dried yielding a porous fibrin matrix. The fibrin matrix of the present invention may be denoted herein as a scaffold, biomatrix or as a sponge, for use as an implant per se, for the culturing of cells or as a cell-bearing tissue replacement implant. Although the examples presented herein refer to the use of the matrix in cartilage repair, it is to be understood that the matrix may be used for tissue reparation and regeneration of many other tissue types including bone, mammary, epithelial, neural, hepatic and endothelial tissue types.

The term "stem cell" as referred to herein refers to an undifferentiated cell that is capable of proliferation. Stem cells are capable of producing either new stem cells or cells called "progenitor cells" that differentiate to produce the specialized cells found in mammalian tissue and organs.

The term "biocompatible" as used herein refers to materials which have low toxicity, clinically acceptable levels of foreign body reactions in the living body, and affinity with living tissues.

The terms "lyophilize" or "freeze drying" refer to the preparation of a composition in dry form by rapid freezing and dehydration in the frozen state (sometimes referred to as sublimation). This process may take place under vacuum at reduced air pressure resulting in drying at a lower temperature than required at full pressure.

The term "residual moisture" as used herein refers to the amount of moisture remaining in the dried sample. It is referred to as a percent of the weight of the sample. In one aspect of the invention the fibrin matrices of the invention have less than 15% residual moisture, preferably less than 10% residual moisture.

The term "cell-bearing" as used herein refers to the capacity of the matrix to allow cells to be maintained within its structure. In one aspect, the cells are able to invade the pores and channels of the matrix and may undergo proliferation and or differentiation.

The term "implantation" refers to the insertion of a sponge of the invention into a patient, whereby the implant serves to replace, fully or partially, tissue that has been damaged, diseased or removed.

The "biologically active" or "bioactive agents" incorporated into the sponge, for example, growth factors, platelet and platelet extracts, angiogenic factors, and the like, are advantageous to, in a non-limiting example, encourage a more rapid growth or differentiation of the cells within the implant, or a more rapid vascularization of the implant. Such factors have now been shown to be effectively retained within the sponge and form a source, or depot, of bioactive agent, for sustained release. Other bioactive agents include antibiotics, enzymes, additional plasma proteins or mixtures thereof.

The "pore size" of a pore within a plasma protein sponge is determined by using the equation: $P=(L \times H)^{1/2}$ wherein, L and H are the average length and height of the pores, respectively, as determined by microscopic analysis of the various sponges.

"Polysaccharides" as used herein refer to complex carbohydrates made of more than one saccharide. Included in the definition are anionic polysaccharides, including non-modified as well as chemical derivatives thereof, that contains one negatively charged group (e.g., carboxyl groups at pH values above about 4.0) and includes salts thereof, such as sodium or potassium salts, alkaline earth metal salts such as calcium or magnesium salts. Non-limiting examples of anionic polysaccharides include pectin, alginate, galactans, galactomannans, glucomannans and polyuronic acids.

A "glycosaminoglycan" or "GAG" as used herein refers to a long unbranched polysaccharide molecules found on the cell surface or extracellular matrix. Non-limiting examples of glycosaminoglycan include heparin, chondroitin sulfate, dextran sulfate, dermatan sulfate, heparan sulfate, keratan sulfate, crosslinked or non-crosslinked hyaluronic acid, hexuronyl hexosaminoglycan sulfate, and inositol hexasulfate. Derivatives, salts and mimetics of the above, including low molecular weight heparin are intended to be included in the invention. Without wishing to be bound to theory, the presence of the GAGs, in particular heparin aids in immobilizing growth factors, in particular heparin binding growth factors such as those of the Fibroblast Growth Factor (FGF) family.

The term "cartilage" as used herein, refers to a specialized type of connective tissue that contains chondrocytes embedded in an extracellular matrix. The biochemical composition of cartilage differs according to type but in general comprises collagen, predominantly type II collagen along with other minor types, e.g., types IX and XI, proteoglycans, other proteins and water. Several types of cartilage are recognized in the art, including, for example, hyaline cartilage, articular cartilage, costal cartilage, fibrous cartilage (fibrocartilage), meniscal cartilage, elastic cartilage, auricular cartilage, and yellow cartilage. The production of any type of cartilage is intended to fall within the scope of the invention. The term "chondrocytes" as used herein, refers to cells which are capable of producing components of cartilage tissue.

The term "variant" as used herein refers to a polypeptide sequence that possesses some modified structural property of the wild type or parent protein. For example, the variant may be truncated at either the amino or carboxy terminus- or both termini or may have amino acids deleted, inserted or substituted. It may be antagonistic or agonistic with respect to normal properties of the native protein. The variant may have similar or altered activity as compared to that of the wild type protein.

Embodiments of the Invention

The present invention relates to porous, freeze-dried fibrin matrices comprised of plasma proteins substantially devoid of exogenous anti-fibrinolytic agents useful for supporting cell growth. The present invention relates to the unexpected finding that a porous, freeze-dried fibrin matrix comprised of plasma proteins substantially devoid of plasminogen exhibits superior biological characteristics, in particular cell viability and cell proliferation. Plasminogen is a plasma protein which is enzymatically converted to an active serine protease, plasmin, having fibrinolytic activity. This activity results in the rapid degradation of fibrin in fibrin clots and matrices. Anti-fibrinolytic agents are typically incorporated into fibrin clots and matrices in order to maintain the integrity of the substrate. The matrices of the present invention lack plasminogen thus obviating the need for exogenous anti-fibrinolytic agents, which have been shown to be deleterious to cells and tissue and which may induce adverse reactions in patients. It is now further disclosed that matrices comprising partially purified plasma proteins also obviate the need for exogenous anti-fibrinolytic agents. The compositions and methods of the present invention are effective in in vivo and in vitro applications including as fully biocompatible implants for tissue engineering as well as in biotechnology. The matrices according to the present invention may be used clinically, per se or as cell-bearing implants. They are true three-dimensional structures capable of providing support and of maintaining cell growth and differentiation.

In one aspect, the present invention relates to a freeze-dried fibrin matrix comprising plasma proteins substantially devoid of exogenous anti-fibrinolytic agents, plasminogen and of organic chelating agents. Substantially devoid of plasminogen refers to plasma proteins comprising less than about 20% plasmin or plasminogen normally present in plasma, preferably less than about 10% of plasminogen normally present in plasma, more preferably less than about 5% of plasminogen normally present in plasma.

The inventors have discovered that a porous freeze-dried fibrin matrix comprising plasma proteins substantially devoid of exogenous anti-fibrinolytic agents, plasminogen and of organic chelating agents provides a superior matrix for clinical and biotechnological applications. In addition to eliminating the need for exogenous anti-fibrinolytic agents and their concomitant detrimental effects, the inventors now show that the fibrin matrix of the present invention is superior as a scaffold for cell seeding, growth and differentiation and tissue repair and regeneration.

According to one embodiment of the present invention, the fibrin matrix comprises plasma proteins, the major protein being fibrin. Fibrin is obtained by the interaction of the plasma proteins fibrinogen (Factor I) and thrombin in the presence of calcium ions ($Ca^{+2}$) and Factor XIII or another fibrin stabilizing factor, to form a fibrin clot. The plasma proteins utilized in the present invention may be purified from a plasma source or may be used from a commercially available source, including native or recombinant proteins, in the substantial absence of organic chelating agents. Total blood, blood fractions, blood derivative, cryoprecipitate, recombinant proteins, plasma or plasma fractions may serve as a plasma protein source for the fibrin sponge of the present invention. The plasma source may be allogeneic or autologous. Another source of the plasma proteins, specifically of fibrinogen, includes fibrinogen variants, including the high molecular weight (HMW), the low molecular weight (LMW) and the LMW derivative (LMW') variants, for example as disclosed in PCT patent application WO 03/087160.

The plasma proteins are substantially devoid of plasminogen. Plasminogen may be removed from the plasma by methods known in the art. In one non-limiting example, the plasminogen is removed from plasma by affinity purification. Epsilon amino carboxylic acid (EACA) ligands as well as lysine resin have been used to purify plasminogen from whole plasma. PCT patent application WO 02/095019 discloses a method for specifically removing plasminogen and plasmin in the presence of fibrinogen from a mixture such as blood or cryoprecipitate. The method requires contacting the mixture comprising plasminogen with a rigid amino acid, such as tranexamic acid, wherein the amino group and carboxylic group are about 7 angstroms apart and the rigid amino acid is covalently bound to the support via the amino group. PCT patent application WO 95/25748 discloses a topical fibrinogen complex essentially free of plasminogen whereby the plasminogen was removed using a Sepharose®-lysine column. Alternatively, some or all of the plasma proteins may be recombinant and consequentially devoid of plasminogen, for example as disclosed in PCT publication WO 99/56797.

The plasma proteins are further substantially devoid of exogenous anti-fibrinolytic agents, which have been shown to be detrimental to cell growth and may induce adverse reactions in patients. Surprisingly, a matrix comprising partially purified plasma proteins also obviates the need for exogenous anti-fibrinolytic agents.

The fibrin matrix of the invention may be used per se, comprising plasma proteins substantially devoid of exogenous anti-fibrinolytic agents, plasminogen and of organic chelating agents, for clinical and biotechnological applications. It may however, further comprise additives that impart other advantageous biological, physical and mechanical characteristics to the matrix. Copending international patent application WO 03/007873 of some of the inventors of the present invention discloses a fibrin matrix comprising plasma proteins and at least one anti-fibrinolytic agent, optionally further comprising agents such as polysaccharides, anionic polysaccharides, glycosaminoglycans, or synthetic polymers added in the preparation to improve certain physical, mechanical and biological properties of the matrix. The incorporation of at least one such agent was shown to impart superior characteristics including elasticity and regular pore size to the sponge.

In one embodiment, the present invention is related to a porous fibrin matrix substantially devoid of exogenous anti-fibrinolytic agents, plasminogen and of organic chelating agents further comprising at least one additive selected from the group consisting of polysaccharides, glycosaminoglycans and synthetic polymers that is useful as a support for culturing or growth of cells, both in vitro and in vivo. The incorporation of at least one additive to the matrix forming materials, results in a sponge having certain advantageous properties including physical, mechanical and/or biological properties. The incorporation of at least one glycosaminoglycan is shown to impart superior characteristics including elasticity to the sponge. The sponges formed are substantially homogeneous having no particles or interrupting substructures other than the pores and interconnecting channels.

In one embodiment the additive may be added ab initio, during formation of the clot. In another embodiment the additive may be introduced to the matrix anytime following formation of the sponge. According to various embodiments of the present invention, the matrix is prepared using at least one glycosaminoglycan selected from the group consisting of crosslinked hyaluronic acid, non-crosslinked hyaluronic acid, heparin and heparin derivatives and mimetics, chondroitin sulfate, dextran sulfate, dermatan sulfate, heparan sulfate and keratan sulfate. In one aspect the glycosaminoglycan is incorporated into the matrix during initial formation of the clot. In one embodiment the glycosaminoglycan is hyaluronic acid. The glycosaminoglycan is added to a final concentration that imparts suppleness and elasticity to the sponge and precludes the need for adjusting the moisture content of the final composition. Hyaluronic acid may be crosslinked or non-crosslinked, having a variety of different molecular weights and may originate from an animal source or a recombinant source. According to one embodiment the concentration of non-crosslinked hyaluronic acid is about 0.005% to about 0.5% final (v/v) more preferably about 0.05% to about 0.1%. In another embodiment the concentration of crosslinked hyaluronic acid is about 0.001% to about 0.1% and more preferably around 0.05% to about 0.09% final concentration. According to one embodiment the glycosaminoglycan is selected from heparin and a derivative thereof.

According to yet another embodiment the present invention may further include the incorporation of an additional synthetic or natural polymer prior to formation of the clot which may modify certain properties of the sponge including physical, mechanical and/or biological properties. These may impart superior characteristics including elasticity, regular pore size and strength to the sponge. Non-limiting examples of natural polymers include cellulose, pectin, polyuronic acids, hexuronyl hexosaminoglycan sulfate and inositol hexasulfate.

The synthetic polymers useful for the present invention may be non-biodegradable or biodegradable. Examples of non-degradable materials include polytetrafluoroethylene, perfluorinated polymers such as fluorinated ethylene propylene, polypropylene, polyethylene, polyethylene teraphthalate, silicone, silicone rubber, polysufone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Examples of degradable materials include hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials. Other components include surfactants including lecithin.

In one embodiment, the invention provides a heterogeneous sponge comprising particulate matter such as calcium phosphate crystals or other particles. The particulate matter may be incorporated ab initio in order to provide a matrix having physical or biological characteristics advantageous for certain applications.

Bioactive Agents

In one embodiment the matrix of the invention further comprises at least one bioactive agent, such as a cytokine, a growth factor and their activators, platelets, a bioactive peptide etc. Without wishing to be bound by theory, incorporation of such agents into the sponge of the present invention provides a slow-release or sustained-release mechanism. As the matrix degrades in vivo, the bioactive agents are released into the surrounding milieu. For example, growth factors, structural proteins or cytokines which enhance the temporal sequence of wound repair, enhance angiogenesis, alter the rate of proliferation or increase the metabolic synthesis of extracellular matrix proteins are useful additives to the matrix of the present invention. The bioactive proteins of the invention are polypeptides or derivatives or variants thereof, obtained from natural, synthetic or recombinant sources, which exhibit the ability to stimulate DNA synthesis and cell division or differentiation of a variety of cells, including primary fibroblasts, embryonal stem cells (ESC), adult stem cells, chondrocytes, vascular and corneal endothelial cells, osteoblasts, myoblasts, smooth muscle and neuronal cells. Representative proteins include bone growth factors (BMPs, IGF) and fibroblast growth factors and their variants, including FGF2, FGF4, FGF9 and FGF18 for bone and cartilage healing, cartilage growth factor genes (CGF, TGF-β) for cartilage healing, nerve growth factor genes (NGF) and certain FGFs for nerve healing, and general growth factors such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF) and other proteins which may enhance the action of the growth factors including heparin sulfate proteoglycans (HSPGs) their mimetics such as dextran sulfate, sucrose octa sulfate or heparin, and fragments thereof. Other factors shown to act on cells forming bone, cartilage or other connective tissue include retinoids, growth hormone (GH), and transferrin. Proteins specific for cartilage repair include cartilage growth factor (CGF), FGFs and TGF-β.

Other biologically active agents that may be included into the matrix include blood platelets, platelet supernatants or extracts and platelet derived proteins, hormones, analgesics, anti-inflammatory agents, anti-microbials or enzymes. Bioactive agents including platelets and platelet supernatant or extract promote the proliferation and differentiation of skeletal cells including chondrocytes and osteoblasts and of other cell types including but not limited to hepatocytes and endothelial cells. Bioactive agents belonging to the class of anti-microbial or anti-inflammatory agents may accelerate the healing process by minimizing infection and inflammation.

Enzymes such as chondroitinase or matrix metalloproteinases (MMPs) may be incorporated to aid in the degradation of cartilage, thus stimulating release of cells into the matrix and the surrounding milieu. In one non-limiting example, the at least one bioactive agent, added ab initio or at any stage following preparation, may be selected to enhance the healing process of the injured or diseased tissue.

According to one embodiment of the present invention the at least one bioactive agent is a therapeutic protein selected from the group consisting of growth factors and their variants. In one embodiment, the growth factor is a fibroblast growth factor (FGF) or bone morphogenetic protein (BMP) or variant thereof. In another embodiment, the FGF is an FGF or FGF variant having the capacity to induce cartilage and bone repair and regeneration and or angiogenesis. The growth factors may be incorporated at a wide range of concentrations, depending on the application. For certain applications sustained release of a bioactive agent is preferred. Sustained release of a bioactive agent may depend on several factors including growth factor concentration, type of glycosaminoglycan incorporated and thrombin concentration.

In contrast to the bioabsorbable heteromorphic sponge of the art, the present inventors now disclose a freeze-dried homogenous fibrin sponge compromising plasma proteins substantially devoid of plasminogen and of organic chelating agents further comprising at least one additive selected from the group consisting of polysaccharides, glycosaminoglycans and synthetic polymers and at least one bioactive agent providing phasic release of said bioactive agent.

According to various specific embodiments of the present invention the porous fibrin matrix comprising plasma proteins substantially devoid of antifibrinolytic agents, plasminogen further comprises at least one glycosaminoglycan and at least one bioactive agent, wherein the bioactive agent is a therapeutic protein belonging to the FGF family of growth factors. In one embodiment a porous fibrin matrix comprising plasma proteins substantially devoid of plasminogen and of organic chelating agents further comprises hyaluronic acid, heparin and an FGF. In one aspect the hyaluronic acid and the heparin or heparin mimetic are incorporated into the sponge ab initio.

According to one non-limiting example the present invention provides a porous homogenous freeze-dried fibrin matrix comprising plasma proteins substantially devoid of plasminogen, substantially devoid of organic chelating agents, further comprising at least one glycosaminoglycan and at least one bioactive agent, wherein the at least one glycosaminoglycan is heparin and the at least one bioactive agent is a therapeutic protein belonging to the FGF family of growth factors or a variant thereof. This sponge provides phasic release of the FGF from the matrix and may be beneficial in certain therapeutic applications. Optionally, at least one bioactive agent may be added to the cell, either in culture or during seeding, for example, to enhance a therapeutic effect.

Additionally, cells genetically engineered to express the aforementioned proteins are including in the present invention. According to one aspect, periosteal cells, mesenchymal stem cells or chondrocytes are used per se or are transfected with cartilage growth factor genes selected from a group including transforming growth factor-β (TGF-β), certain FGFs or CGF for cartilage repair and regeneration; for bone repair periosteal or other mesenchymal stem cells or osteoblasts are used per se or are transfected with bone growth factor genes selected from a group including bone morphogenetic protein (BMP) family genes or fibroblast growth factor family genes; for nerve repair neural cells and neural support cells are used per se or are transfected with genes selected from a group including nerve growth factor (NGF) gene or specific FGFs.

Furthermore, specific enzymes maybe admixed with the sponge of the invention in order to promote degradation of the proteoglycans and/or proteins present in the cartilage. Chondrocytes of the cartilage are embedded in the thick extracellular matrix (ECM) of the joint. Without wishing to be bound by theory enzymes known in the art including collagenase, trypsin, chymotrypsin, chondroitinase of the various types, are able to degrade the ECM of the surface of the joint, thereby releasing chondrocytes that are able to invade the sponge of the invention to promote cartilage regeneration.

The matrix of the invention, in certain embodiments may further include one or more antiseptics, such as methylene blue, and/or one or more drugs including antimicrobials such as antibiotics and antiviral agents; chemotherapeutic agents; anti-rejection agents; analgesics and analgesic combinations; anti-inflammatory agents; adhesion protein such as fibronectin or fragments thereof and hormones such as steroids.

According to one embodiment the at least one bioactive agent is platelets or platelet supernatant. The platelets may be present in the plasma protein concentrate or may be added exogenously. An exogenous source of platelets is added during the clot forming process to a final concentration of 0.1% to 30% of final sponge volume, more preferably 5% to 25% of final sponge volume. An exogenous source of platelet supernatant is added during the clot forming process to a final concentration of 0.1% to 30% of final sponge volume, more preferably 1% to 15% of final sponge volume.

Applications

The porous homogeneous fibrin matrix of the invention is useful as scaffold for tissue engineering applications. The absence of plasminogen obviates the need for external antifibrinolytic agents and thus results in a sponge that is fully biocompatible. The optional presence of the bioactive agents and the glycosaminoglycan together provides as an unexpectedly advantageous support for cellular growth in vitro and in vivo.

The in vivo uses of the plasma matrix are manifold. The fibrin scaffold may be used as an implant per se, for providing mechanical support to a defective or injured site in situ and/or for providing a matrix within which cells from the defective or injured site proliferate and differentiate. The cells may be stem cells or progenitor cells or may be specialized cells such as chondrocytes, osteoblasts, hepatocytes, or mesenchymal, endothelial, epithelial, urothelial, endocrine, neuronal, pancreatic, renal or ocular cell types.

The homogeneous porous fibrin matrix of the present invention can be utilized in reconstructive surgery methods for regenerating and/or repairing tissue that have been damaged for example by trauma, surgical procedures or disease. The present invention provides a matrix for use as an implantable scaffold per se for tissue regeneration. According to one aspect of the invention, the matrix serves as both a physical support and an adhesive substrate for in vivo cell growth. As the cell populations grow and the cells function normally, they begin to secrete their own extracellular matrix (ECM) support. The scaffold polymer is selected to degrade as the need for an artificial support diminishes.

Scaffold applications include the regeneration of tissues such as neuronal, musculoskeletal, cartilaginous, tendonous, hepatic, pancreatic, renal, ocular, arteriovenous, urinary or any other tissue forming solid or hollow organs. Some typical orthopedic applications include joint resurfacing, meniscus repair, non-union fracture repair, craniofacial reconstruction or repair of an invertebral disc.

The porous fibrin matrix of the invention is useful, inter alia, as an unexpectedly advantageous support for cellular growth. The absence of exogenous anti-fibrinolytic agents results in a fibrin matrix that is fully compatible with in vitro and in vivo cell growth, proliferation and differentiation. An additional advantage of the fibrin matrix of the invention is its improved ability to absorb cells and retain them. The need to wet or wash the sponge of the invention prior to cell seeding is precluded by the absence of exogenous anti-fibrinolytic agents. In one embodiment the matrix of the invention serves as a scaffold for the growth, proliferation and/or differentiation of cells including stem cells, progenitor cells or other cell types including chondrocytes, osteoblasts, hepatocytes, mesenchymal, epithelial, urothelial, neuronal, pancreatic, renal or any other cell types which it is desired to culture within a three dimensional support.

In a certain embodiment of the present invention cells may be cultured on the matrix for subsequent implantation. Stem cells derived from any tissue or induced to differentiate into a specific tissue type may be utilized. Preferably the cells are derived from autologous tissue. For example, for culturing cartilage, chondrocytes or mesenchymal stem cells may be seeded on the matrix. In specific embodiments of the invention, chondrocytes or chondrocyte progenitor cells can be seeded on the matrix prior to implantation or at the site of implantation in vivo. The sponge is useful for the delivery of cells in situ to a specific site in the body, such as dopamine expressing cells to Parkinson's patients.

Additionally, the cell of interest may be engineered to express a gene product which would exert a therapeutic effect, for example anti-inflammatory peptides or proteins, growth factors having angiogenic, chemotactic, osteogenic or proliferative effects. A non-limitative example of genetically engineering cells to enhance healing is disclosed in U.S. Pat. No. 6,398,816.

According to certain embodiments of the invention, the fibrin matrix is used as a support for chondrocyte growth and as a scaffold for neo cartilage formation. However, the plasma matrix of the invention may be used as a surface useful for tissue culture for any suitable cells, such as mesenchymal cells or other tissue forming cells at different levels of potency. For example, cells typically referred to as "stem cells" or "mesenchymal stem cells", are pluripotent, or lineage-uncommitted cells, which are potentially capable of an unlimited number of mitotic divisions to either renew a line or to produce progeny cells with the capacity to differentiate into any cell type can be grown on the matrix of the invention. In addition, lineage-committed "progenitor cells" can be grown on the matrix of the invention. A lineage-committed progenitor cell is generally considered to be incapable of an unlimited number of mitotic divisions and will eventually differentiate only into a specific cell type. Cell types include chondrocytes, osteoblasts, hepatocytes, or mesenchymal, endothelial, epithelial, urothelial, endocrine, neuronal, pancreatic, renal or ocular cell types.

In yet further embodiments of the invention, the porous homogeneous fibrin matrix can be utilized as a coating of synthetic or other implants or medical devices. The matrix of the invention may be applied to prostheses such as pins or plates by coating or adhering methods known to persons skilled in the art. The matrix coating, which is capable of supporting and facilitating cellular growth, can thus be useful in providing a favorable environment for the implant or prosthesis.

A person skilled in the art can adjust the procedures exemplified below in accordance with specific tissue requirements. For example, for cartilage repair the porous, homogeneous freeze-dried fibrin matrix of the invention may be used in conjunction with other therapeutic procedures including chondral shaving, laser or abrasion chondroplasty, and drilling or microfracture techniques.

Preferably, the fibrin sponge is implanted per se, and serves as a scaffold for cellular growth in situ. Alternatively, the matrix is seeded with desired cells, the cells allowed to proliferate and the sponge comprising the cells implanted at a site in need of tissue repair or regeneration. The glycosaminoglycan enriched homogeneous fibrin matrix, in its dry form, adheres exceptionally well to tissue surfaces. According to one embodiment of the present invention a dry sponge of the invention, or another type of bioabsorbable matrix, is placed on the area where tissue regeneration is desired. A second sponge, onto which particular cells were cultured, is placed on top of the dry sponge. The wetted sponge of the invention adheres well to the dry sponge of the invention or another matrix. During the healing process, the cells from the sponge onto which the cells were originally seeded migrate into the matrix adhering directly to the area of tissue regeneration.

In the reconstruction of structural tissues like cartilage and bone, tissue shape is integral to function, requiring the molding of the matrix into three dimensional configuration articles of varying thickness and shape. Accordingly, the matrix of the invention may be formed to assume a specific shape including a sphere, cube, rod, tube or a sheet. The shape is determined by the shape of a mold, receptacle or support which may be made of any inert material and may be in contact with the matrix on all sides, as for a sphere or cube, or on a limited number of sides as for a sheet. The matrix may be shaped in the form of body organs or parts and constitute prostheses. Removing portions of the matrix with scissors, a scalpel, a laser beam or any other cutting instrument can create any refinements required in the three-dimensional structure.

The matrix according to further embodiments of the invention can be used as a matrix for growing cells or tissue culture in vitro. The matrices of the invention provide a relatively large surface area for cells to grow on and a mechanically improved scaffold for implantation.

The methods for seeding cells on the matrix are manifold. In a non-limiting example, the cells are adsorbed by placing the cells on the surface of the matrix or absorbed into the matrix by placing the sponge in a solution containing cells. The matrix may be seeded with the desired cells by surface seeding, at a density of about $10^4$ cells per $cm^3$, more preferably about $10^5$ cells per $cm^3$.

It will be appreciated that the matrix of the invention can support the growth and/or implantation of any type of cartilage or other suitable tissue. Furthermore, although the invention is directed predominantly to methods for growth and/or implantation of tissue in humans, the invention may also include methods for growth and/or implantation of tissues in any mammal.

Furthermore, the sponge of the present invention may be used as a component of a two-phase or multi-phase material for tissue repair such as seen in osteochondral defects. In a non-limiting example, one layer may comprise a calcium phosphate material whilst an additional layer may comprise the sponge of the invention. Gao et al. (Tissue Engin. 8:827-837, 2002) describes a method for the repair of osteochondral defects in rabbit knees using a composite material comprising an injectable calcium phosphate and a hyaluronic acid sponge.

Method of Matrix Preparation

The present invention provides a method for preparing a porous homogeneous fibrin matrix. The matrix forming solutions include a thrombin solution and a plasma protein solution. As used herein the thrombin solution comprises thrombin in an amount sufficient to cleave fibrinogen and yield a fibrin matrix in the presence of calcium ions ($Ca^{+2}$) ions. The plasma proteins may derive from a commercial, xenogeneic, allogeneic or autologous source and comprise fibrinogen and factor XIII, substantially devoid of plasminogen and in the substantial absence of organic chelating agents. The plasma protein solution may comprise fibrinogen variants such as the high molecular weight or low molecular weight variants.

According to one embodiment of the present invention the porous homogeneous fibrin sponge is prepared by transferring the thrombin solution into a mold, adding the plasma protein solution; freezing the clotted mixture and lyophilizing. Alternatively, the plasma proteins are mixed with thrombin in the presence of calcium ions under conditions suitable for achieving clotting; the mixture is cast or mold in a solid support prior to achieving clotting; the clotted mixture is frozen and lyophilized. It is to be understood that when incorporated, additives and bioactive agents are added independently to either of the matrix forming solutions, i.e. the plasma proteins or to the thrombin solution, prior to the formation of the clot or are placed into the mold prior to, concurrently with or following addition of the thrombin.

A method for preparing a porous freeze-dried fibrin matrix formed from plasma proteins having less than 10% residual moisture and being substantially devoid of exogenous anti-fibrinolytic agents and of organic chelating agent comprises the following steps:

providing a thrombin solution and a plasma protein solution wherein the plasma protein solution is substantially devoid of exogenous anti-fibrinolytic agents and of organic chelating agents;

introducing the thrombin solution and the plasma protein solution to a solid receptacle or mold in the presence of calcium ions;

incubating under conditions appropriate to achieve clotting;

freezing the clotted mixture; and lyophilizing the clotted mixture, to obtain a sponge.

According to one embodiment of the present invention the plasma proteins are partially purified plasma proteins. According to another embodiment of the present invention the plasma proteins are devoid of plasminogen. According to yet another embodiment the plasma protein solution comprising less than about 20% of plasminogen normally present in blood plasma, preferably less than about 10% of the plasminogen normally present in plasma and more preferably less than about 5% of the plasminogen normally present in plasma.

According to one embodiment the matrix of the invention may be prepared by sequential introduction of the thrombin solution and plasma protein solution into the mold or solid receptacle. Either solution may be introduced first. According to another embodiment of the present invention the thrombin solution and the plasma protein solution are mixed together and subsequently introduced into a mold. The resulting sponges are different in their porosity and cell dispersion.

A method for preparing a porous freeze-dried fibrin matrix having less than 10% residual moisture and being substantially devoid of exogenous anti-fibrinolytic agents, and of organic chelating agents further comprising at least one additive selected from the group consisting of polysaccharides, glycosaminoglycans and synthetic polymers comprises the following steps:

providing a plasma protein solution substantially devoid of exogenous anti-fibrinolytic agents and of organic chelating agents and a thrombin solution and wherein at least one of the plasma protein solution or the thrombin solution contains at least one additive selected from the group consisting of polysaccharides, glycosaminoglycans and synthetic polymers;

introducing the thrombin solution and the plasma protein solution to a solid receptacle or mold;

incubating under conditions appropriate to achieve clotting;

freezing the clotted mixture;

lyophilizing the clotted mixture, to obtain a sponge;

The sponge may further comprise at least one bioactive agent, added ab initio to either the thrombin solution or the plasma protein solution.

According to one embodiment of the present invention the plasma proteins are partially purified plasma proteins. According to another embodiment of the present invention the plasma proteins are devoid of plasminogen. According to yet another embodiment the plasma protein solution comprising less than about 20% of plasminogen normally present in blood plasma, preferably less than about 10% of the plasminogen normally present in plasma and more preferably less than about 5% of the plasminogen normally present in plasma.

According to various embodiments of the present invention plasma proteins at a concentration of about 20 mg/ml to about 50 mg/ml, substantially devoid of exogenous anti-fibrinolytic agents, plasminogen and of organic chelating agents are mixed with hyaluronic acid and/or heparin and the mixture is added to the thrombin solution in the solid support to achieve formation of a clot. The clot is frozen and lyophilized.

According to another embodiment a plasma protein solution comprising plasma proteins at a concentration of about 20 to about 50 mg/ml, substantially devoid of antifibrinolytic agents and substantially in the absence of organic chelating agents, comprising hyaluronic acid and heparin bound to FGF are mixed and the mixture added to the thrombin solution in the solid support to achieve formation of a clot. The clot is frozen and lyophilized.

The final concentration of thrombin may be varied in order to produce sponges with distinct biological, physical and mechanical features useful for different applications. Thrombin concentrations of about 0.5 IU/ml to about 2 IU/ml provide sponges with similar properties in terms of cell viability and growth. Other concentrations, as low as 0.15 IU/ml may be useful as well, depending on the application.

In its final form prior to use with cells the sponge is substantially dry and contains less than 15% residual moisture, more preferably less than 10% residual moisture.

Yet another aspect of the present invention provides methods of treatment and use of the fibrin matrix of the invention for treating injured or traumatized tissue, including cartilage and bone defects. The method of treatment described herein is advantageous in that it requires minimal preparation for use by the medical practitioner. The in vivo uses of the porous fibrin matrix are manifold. The porous fibrin matrix may function as a scaffold and may be used as an implant per se, for providing mechanical support to a defective or injured site in situ and/or for providing a matrix within which cells from the defective or injured site proliferate and differentiate. For example, for cartilage repair the porous fibrin matrix may be used in conjunction with other therapeutic procedures including chondral shaving, laser or abrasion chondroplasty, and drilling or microfracture techniques.

The porous fibrin matrix of the invention, being an effective scaffold supporting cell growth, may further be utilized in vivo in reconstructive surgery, for example as a matrix for regenerating cells and tissue including neuronal cells, cardiovascular tissue, urothelial cells and breast tissue. Some typical orthopedic applications include joint resurfacing, meniscus repair, non-union fracture repair, craniofacial reconstruction, osteochondral defect repair or repair of an invertebral disc. The fibrin matrix of the invention may serve to treat defects resulting from disease such as osteoarthritis. The components of the matrix may be cast into a mold specifically designed for a distinct lesion or defect. In a non-limiting example, the mold may be prepared by computer aided design. In other instances the medical practioner may have to cut or slice the sponge to fit a particular lesion or defect. The matrix of the invention is particularly beneficial for minimally invasive surgical techniques such as a mini-arthrotomy or arthroscopy and overcomes the need for fully open joint surgery.

In one embodiment, the porous fibrin matrix may be used as a coating on synthetic or other implants such as pins and plates, for example, in hip replacement procedures. Thus, the present invention further provides implants or medical devices coated with the comprising the porous fibrin matrix of the invention.

Furthermore, the sponge of the present invention may be used as a component of a two-phase or multi-phase material for tissue repair such as seen in osteochondral defects. In a non-limiting example, one layer may comprise a calcium phosphate material whilst an additional layer may comprise the sponge of the invention.

The plasma protein solution may be from a commercial source, natural or recombinant proteins, or may be prepared from plasma. According to one embodiment of the present invention the plasma protein solution derives from allogeneic plasma. According to another embodiment of the present invention, at least one of the components, preferably the plasma proteins, used for preparing the matrix derives from autologous plasma or recombinant proteins. According to another embodiment of the present invention, all of the plasma components used in preparing the matrix are autologous. The plasma proteins may be isolated by a variety of methods, as known in the art and exemplified herein below, resulting in a fibrin matrix having substantially similar properties, as measured by pore size, elasticity, compression and cell bearing capabilities. A stable thrombin component may be isolated from autologous plasma, according to methods known in the art for example those disclosed in U.S. Pat. No. 6,274,090 and Haisch et al (Med Biol Eng Comput 38:686-9, 2000).

The resulting fibrin matrix exhibits advantageous properties including biocompatibility, pore size compatible with cell invasion and proliferation and ability to be molded or cast into definite shapes.

In one aspect, blood is drawn from a patient in need of tissue repair or regeneration, plasma proteins, are isolated from the autologous plasma and a matrix prepared thereof. The platelets are optionally isolated and returned to the plasma. The matrix of the present invention may serve as an implant for use as a scaffold per se or as a cell-bearing scaffold for in vivo implantation.

According to one embodiment of the present invention a porous fibrin sponge produced from a fibrinogen solution, wherein the fibrinogen solution is subjected to dialysis with a solution not requiring a complexing agent, serves as a scaffold for the growth of cells in vitro and in vivo. According to another embodiment the fibrin sponge is formed by the action of a thrombin solution on the dialyzed fibrinogen solution and subsequently subjected to freeze drying.

While not wishing to be bound by any particular theory the substantial absence of organic complexing agents may provide the matrix of the present invention with properties beneficial to the proliferation and metabolism of certain cell types. As shown in the examples herein, the matrix of the present invention supports the proliferation of cartilage cells in both in vivo and in vitro systems.

The presence of certain organic complexing agents in a range of 1 to 20 mM, necessary for the production of a flexible fibrin web disclosed in U.S. Pat. No. 6,310,267 for wound healing, may in itself have a detrimental effect on the proliferation of certain cell types. The use of a fibrin web for cell growth and proliferation, in vivo or in vitro, has not been disclosed. Nevertheless, it may be possible to culture certain types of cell types using the webs of the aforementioned patent.

According to one embodiment of the present invention heparin is incorporated into the matrix to a final concentration of about 0.1 ug/ml to about 1 mg/ml. In another embodiment the concentration of heparin is about 1 ug/ml to about 50 ug/ml. As used herein ug/ml refers to a microgram per milliliter.

According to another embodiment of the present invention crosslinked hyaluronic acid is incorporated into the matrix to a final concentration of about 0.001% to about 0.1%, more preferably about 0.05% to about 0.09%.

According to another embodiment of the present invention non-crosslinked hyaluronic acid is incorporated into the matrix to a final concentration of about 0.005% to about 0.5%, more preferably about 0.05% to about 0.1%.

According to yet another embodiment of the present invention both heparin and hyaluronic acid are incorporated into the matrix at respective concentration ranges.

Surprisingly, in view of the known function of heparin as an anti-coagulant, it is now disclosed that the incorporation of heparin into the matrix does not interfere with either the formation of the matrix or the therapeutic benefits of the matrix. Without wishing to be bound by theory, heparin serves primarily to bind FGF or other therapeutic proteins and creates a depot for sustained release of said proteins. In addition, low molecular weight fragments of heparin released from the matrix may function as anti-inflammatory agents and assist in the healing process of diseased or traumatized tissue (U.S. Pat. Nos. 5,474,987; 5,686,431; 5,908,837).

The following examples are intended to be merely illustrative in nature and to be construed in a non-limitative fashion.

EXAMPLES

Example 1

Preparation of a Fibrin Matrix

Although detailed methods are given for the preparation of the plasma protein, it is to be understood that other methods of preparing plasma proteins are known in the art and are useful in the preparation of the matrix of the present invention. A non-limiting example of a protocol for the preparation of a fibrinogen-enriched solution is given in Sims, et al. (Plastic & Recon. Surg. 101:1580-85, 1998). Any source of plasma proteins may be used, provided that the plasma proteins are processed to be substantially devoid of anti-fibrinolytic agents, plasminogen and of organic chelating agents Examples of plasma protein preparation methods are given in examples 2 and 3, hereinbelow.

Materials and Methods:

Source of plasma proteins e.g. Plasminogen-free fibrinogen (Omrix, Ill.) approximately 50-65 mg/ml stock solution.

Calcium Chloride 5 mM

Thrombin (1000 International Units/ml, Omrix, Ill.)

Optional: Hyaluronic acid; crosslinked (Hylan (Synvisc), approx. MW $6\times10^6$, Genzyme, US) or non-crosslinked (approx. MW $8\times10^5$, MTF, US; approx. MW $3.6\times10^6$, BTG, IL)

The concentration of thrombin determines the reaction time for the polymerization of the fibrin monomers and contributes to the pore size and fiber thickness of the final sponge. A concentration of about 0.15 IU to about 15 IU thrombin/mg plasma proteins yielded a sponge with good physical and biological properties. The concentrations of about 1 to about 1.5 IU thrombin/mg plasma proteins was chosen because it gave a fast reaction but allowed adequate time for pouring the two solutions (plasma protein and thrombin) before the reaction completes. It should be noted that other concentrations are acceptable for obtaining a matrix with substantially similar properties. For convenience, as used herein 1.5 IU thrombin/mg total protein is the equivalent of about 30 IU thrombin/ml.

The plasma protein solution and the thrombin solution were mixed together in a ratio of approximately 2:1 (for example 210 μl plasma protein and 90 μl thrombin solution) in the following order: A 48 well ELISA plate was coated with 90 μl of thrombin solution, and the plasma protein solution was added. Alternatively, a 96 well ELISA plate was used and about 19.5 ul thrombin solution was added to the wells followed by the addition of about 45.5 ul plasma protein; or for a slightly thicker matrix about 24 ul thrombin solution and 51 ul plasma protein. The mixture was incubated at room temperature (~25° C.) for about 10 minutes or until the clot formed, followed by freezing at about −60° C. to about −90° C. from about 30 minutes to several days. The 48 well size sponges were lyophilized for about 5 hours while the 96 well plate sponges were lyophilized for about 4 hours. The 96 well plate yields sponges of about 5 mm diameter and the 48 well plate yields sponges of about 10 mm (1 cm) diameter (about 0.8 cm$^2$).

A 35 mm diameter sponge has been prepared for the repair of larger defects, such as those that may develop in osteoarthritis. A 35 mm sponge (about 9.5 cm$^2$, about 2 to about 2.5 cm$^3$) was prepared by mixing 2 ml plasma protein solution with 1 ml thrombin, casting into an appropriate mold, such as a 35 mm petri dish or a 6-well cell culture plate, frozen and lyophilized at −40° C. for about 12 hours. The fibrin sponges were prepared under aseptic conditions. It is to be noted that the solutions may be cast into a mold of any desired shape. The sponge that resulted was a fleece-like matrix.

According to other embodiments of the present invention the matrix is prepared with certain additives including polysaccharides, glycosaminoglycans and synthetic polymers. Biological, mechanical and physical parameters were shown to be controlled by incorporating those additives. All additives were filtered (0.2 μm) and were added to the plasma protein solution. When hyaluronic acid was incorporated in the matrix, the plasma protein solution and hyaluronic acid solution were incubated together before casting. A non-limiting sample list of the additives and concentrations tested are shown in the Table 1 below:

TABLE 1

| Additive | % final concentration |
| --- | --- |
| Glycerol | 0.005; 0.01; 0.05; 0.1; 0.5; 1 |
| Crosslinked (X-linked) HA | 0.0024; 0.012; 0.024; 0.05; 0.10; 0.5 |
| Non-X-linked HA | 0.002; 0.02; 0.05; 0.07; 0.08; 0.09; 0.1; 0.11; 0.13 |
| Heparin | 0.05; 0.1; 0.5; 1.0; 2.5; 10 ug/ml final |
| Heparin + Crosslinked HA | Combinations of above |
| Heparin + Non-X-linked HA | Combinations of above |
| Glycerol + HA | Combinations of above |

Note:
Non-X-linked HA refers to non-crosslinked hyaluronic acid.

A therapeutic protein, FGF (about 1 to about 10 ug/0.2 cm$^2$ sponge) was added either to the plasma protein solution or was mixed with heparin and then added to either the plasma protein or thrombin solutions. Experiments have been performed to determine the optimal concentration of the additives in terms of matrix flexibility, elasticity, pore size, sustained release of bioactive agents and cell growth capacity. The additives impart beneficial properties, including surface, mechanical and/or biological properties, to the sponge during its preparation. Optimization was carried out regarding the concentration of the bioactive agents as well. In one embodiment the bioactive agents include growth factors, platelet supernatant, native platelets, platelet membranes and other materials. According to one embodiment the present invention provides a matrix comprising heparin or a derivarive thereof and hyaluronic acid further comprising FGF or FGF variant. Examples are presented herein below.

Example 2

Isolation of Partially Purified Plasma Proteins from Whole Plasma

Plasma protein may be prepared from different sources such as fresh plasma, fresh frozen plasma, recombinant proteins and xenogeneic, allogeneic or autologous blood. The fresh frozen plasma was received from the blood bank (Tel-Hashomer, Israel). The plasma (220 ml) was thawed in a 4° C. incubator over night, followed by centrifugation at 4° C. at approximately 1900 g for 30 min. The pellet was resuspended in 2.5 ml PBS with gentle rolling until a homogenized solution was seen. The total protein concentration may be estimated by Bradford assay and SDS-PAGE (comparing to a standard). Exemplary samples were found to be about 42 mg total protein/ml to about 50 mg total protein/ml. The plasma may further be treated to remove plasminogen, using methods known in the art. Non-limiting examples of methods useful for removing plasminogen from blood or blood derivates such as plasma or a cryoprecipitate are disclosed in PCT patent publications WO 02/095019 and WO 95/25748.

It is to be understood that the plasma protein source may be xenogeneic, allogeneic or autologous blood. Preferably, the plasma protein source is allogeneic or autologous. A non-limiting method for the isolation of a platelet-enriched plasma is disclosed in U.S. Pat. No. 6,475,175.

Another embodiment of the present invention provides a plasma protein sponge incorporating at least one additive and blood platelets or platelet supernatant. Sponges comprising 0.024% or 0.08% final concentration hyaluronic acid and 1% or 10% final concentration platelet released supernatant or whole platelets were prepared. Platelet supernatant was made by exposing isolated platelets (obtained from the Israel blood bank) to thrombin as described (Gruber et al., Clin Oral Implants Res 13:529-535, 2002), collecting the supernatant and adding it to the plasma protein solution prior to sponge formation. Sponges comprising platelets were prepared by adding platelets directly to the plasma proteins in the following manner: 73 ul platelets and additive (hyaluronic acid to 0.024% or 0.08% final concentration) was added to plasma proteins (30 mg total protein/ml) and the solution brought to 210 ul final volume. The sponge was made as described hereinabove utilizing partially purified plasma proteins.

Example 3

Extraction of Plasma Protein Fractions from Allogeneic or Autologous Blood

Materials:
1) Sodium citrate, 3.8% or any other pharmaceutically acceptable anti-coagulant
2) Ammonium sulfate $(NH_4)_2SO_4$, saturated (500 g/l)
3) Ammonium sulfate $(NH_4)_2SO_4$, 25%
4) Phosphate-EDTA buffer: 50 mM phosphate, 10 mM EDTA, pH 6.6
5) Tris-NaCl buffer: 50 mM Tris, 150 mM NaCl, pH 7.4
6) Ethanol, absolute 4° C.
7) Whole blood (Israel Blood Bank, Tel Hashomer Hospital or from patient)

Methods:
This method may be used to produce plasma proteins that may be treated for removal of plasminogen by methods known in the art, including affinity chromatography. The plasma proteins are isolated according to standard methods. To one 450 ml bag of blood from the blood bank, containing sodium citrate, 50 ml of a 3.8% sodium citrate solution was added and the solution was mixed gently.

The blood-sodium citrate was centrifuged at 2,100 g for 20 min. The supernatant plasma was collected re-centrifuged at 5000 g for 15 min. at 4° C. The supernatant plasma was put on ice, and saturated ammonium sulfate solution was added at a ratio of one volume ammonium sulfate to 3 volumes of supernatant (1:3 volume ratio). The solution was kept at 4° C. for 1.5 hrs with occasional mild shaking (magnetic stirring is not allowed). The supernatant plasma was centrifuged at 5000 g for 15 min at 4° C. The supernatant was discarded and each pellet washed with 10 ml of 25% animonium sulfate solution (pellet not dissolved). Each pellet was dissolved in 6-7 ml of the phosphate-EDTA buffer. A sample, typically 100 µl of the solution, was kept for SDS-PAGE and clotting analyses. The dissolved pellets were pooled and the ammonium sulfate precipitation was repeated by adding saturated ammonium sulfate to the plasma sample to achieve a 1:3 volume ratio (Typically, 25 ml ammonium sulfate to 75 ml plasma). The solution was kept at 4° C. for 1.5 hrs with occasional mild shaking, and centrifuged at 5000 g for 15 min. The supernatant was discarded and the pellets were dissolved in a volume of Tris-NaCl buffer that was equal to or less than the volume of phosphate-EDTA buffer used above. A typical total amount was about 45 ml.

The sample may be dialyzed (SnakeSkin™ dialysis tubes, 3.5 kD cutoff, Pierce) for 3-4 hours or overnight at 4° C. in 1.5 liters of Tris-NaCl buffer. The sample was centrifuged in high-speed resistant tubes at 21,000 g for 15 min at 4° C. to remove any insoluble material. The supernatant was collected and kept on ice.

The supernatant was ethanol precipitated by adding ethanol to a final concentration of 7% and kept on ice for 30 min. The solution was centrifuged at 5000 g for 15 min, the supernatant discarded and the pellet dissolved in the same volume (typically about 45 ml) Tris-NaCl buffer. The solution was dialyzed overnight at 4° C. in 1.5 liter of Tris-NaCl Buffer. The dialyzed solution was centrifuged at 21,000, at 4° C. for 15 min, to eliminate any non-dissolved material.

Protein concentrations were determined using the standard Bradford method. The protein yields ranged from 0.2 to 0.6 mg per ml of full blood, with typical results of about 0.4 to 0.5 mg/ml. Clot formation ability was determined by adding 30 µl thrombin (100 IU/ml; Omrix) to 70 µl plasma product (10 mg/ml), clotting should occur within 30 sec. Protein purity was determined by electrophoretic analysis of 50 µg of the sample on a 5% SDS-polyacrylamide gel and staining using Coommassie blue. The remainder of the supernatant was collected, frozen and lyophilized until dry, 48 hours.

Example 4

Presence of Plasmin and Plasminogen in Plasma Protein Sample

The plasma proteins substantially devoid of plasminogen typically comprised about 9 to about 10 ug plasmin and plasminogen per each milliliter of total protein, as identified by a polyclonal antibody that detects both the plasminogen and plasmin. Human plasma typically comprises approximately 200 mg plasminogen per liter or about 200 ug/ml.

This experiment was designed to determine the concentration of plasmin that could be tolerated in a plasma protein clot. The same experimental design is used for testing the tolerance for plasminogen. Plasminogen is the precursor of the active serine protease plasmin, which is capable of degrading fibrin.

Two concentrations of plasmin (ICN Biomedical, 194198, stock 20 mg/ml), 0.09 mg/ml, 0.045 mg/ml were added to the plasma proteins substantially devoid of plasminogen (Omrix), prior to casting of the solutions. The plasmin concentration of 0.09 mg/ml represents about a ten-fold greater plasmin concentration than the total plasmin and plasminogen concentration present in the commercially available plasma proteins. The plasmin concentration of 0.045 mg/ml represents about a five-fold greater plasmin concentration. The plasma protein solution for the sponge comprising 0.09 mg/ml plasmin was prepared by mixing 281 ul plasma proteins (64 mg/ml), 67.5 ul hyaluronic acid, 2.7 ul plasmin and 251.3 saline. The plasma protein solution for the sponge comprising the 0.045 mg/ml plasmin was prepared by mixing 281 ul plasma proteins, 67.5 ul hyaluronic acid, 1.35 ul plasmin and 250 ul saline. A control without the addition of plasmin was prepared. Five sponges were prepared from each solution by adding 43 ul thrombin to a well (1 IU thrombin/mg plasma proteins) and 87 ul of the plasma protein solution and the mixture allowed to set at room temperature.

Neither of the mixtures comprising plasmin formed a clot, while the plasmin-free control formed a clot within minutes and a freeze dried sponge was formed following freezing and lyophilization. This indicates that the plasma proteins may tolerate less than 45 ug/ml plasmin or less than about 22.5% of the plasminogen and plasmin normally present in plasma.

Example 5

Matrix Morphology and Mechanical Properties

In general, matrices for tissue engineering are characterized according to several criteria, including chemical nature, homogeneity, porosity, adhesion, biocompatibility and elasticity, amongst others (Hunziker, Osteoart. Cart., 10:432-465, 2002). Table II of the aforementioned reference lists several of the properties and the biological basis of these properties.

Several of the aforementioned properties are measured for the matrix of the invention. Porosity, important for cell migration and adhesion is determined by geometrical measurements using the light microscope by sectioning the matrix into thick specimens. Specimens are mounted on slides and are stained by hematoxylin/eosin. An optical micrometer measured the pore size and the distance between neighboring pores.

Scanning Electron Microscope (SEM) Analysis is performed in order to analyze homogeneity and ultra structure of the matrix. The thickness of the fibrin fibers is measured in this way, as well.

Moisture and residual moisture are measured using standard tests, known in the art. In its final form prior to use with cells the sponge is substantially dry and contains less than 15% residual moisture, more preferably less than 10% residual moisture.

Mechanical property measurements are performed, for example, using a Chatillon TCD200 machine with a digital force gauge DF12. Each plasma protein sponge is 2.5 cm long, 0.5 cm wide; and is fully lyophilized. Deformation represents the elasticity of the sponge, i.e. the amount of pull as measured in millimeters (mm) that may be exerted until the sponge tears. Force is calculated in kiloPascal (kPa) and represents the amount of energy required to tear the sponge strips. The thickness of the sponge is taken into consideration when making the calculation.

Example 6

Cell Seeding on the Matrix

Different methods of seeding cells onto the sponge may be used. Important to seeding is cell adherence, migratory capacity and proliferation of cells within the matrix. Cells may be suspended in medium, PBS, or any biocompatible buffer alone or in the presence of bioactive agents. Cells may be seeded by placing a drop of liquid containing cells on the sponge and allowing the cells to adsorb into the sponge. Alternatively, the cells in the liquid may be absorbed into the sponge by placing the sponge in a container holding a suspension of cells. Other methods including spray seeding have also been shown to be effective.

One particular advantage of the present invention is the high level of cell viability and excellent cell distribution following cell seeding directly on a dry sponge. Often a matrix comprising an exogenous anti-fibrinolytic agent such as tranexamic acid exhibits lower cell viability following seeding. The cells seem to recover but the exogenous anti-fibrinolytic agents may be detrimental to initial cell growth. When such a sponge is washed and some or all of the tranexamic acid is removed cell proliferation is improved. It is also noted that many cells settle at the periphery of the matrix following on a wet sponge while there is a better cell distribution following seeding on a dry sponge.

Materials and Methods:

Sponges comprising different concentrations of plasma proteins and thrombin were tested. Sponges comprising 10 mg/ml, 15, 16.5 mg/ml, 18 mg/ml, 20 mg/ml, 22 mg/ml, 25 mg/ml, 30 mg/ml and varying concentrations of hyaluronic acid (from about 0.05% to about 1.1%) and either 1, 1.5 or 2 IU thrombin/mg proteins. A total of about $5 \times 10^5$ to about $5 \times 10^6$ chondrocytes were seeded on 1 cm diameter sponges and allowed to incubate for three days. Different volumes of growth media were added and the cell-embedded matrix allowed to incubate. It is to be understood that the sponge of may be of varying sizes, shapes and thickness.

Following a three-day, 1 week and three week incubation for the seeded sponges, some of the sponges were collagenase degraded and cells counted following trypan blue staining. Cell proliferation is determined as described in Example 8, below.

Samples of the cell-bearing sponges or matrices, were paraffin-embedded and sections prepared using a microtome. The histological sections are further stained using different biological stains including hematoxylin and eosin (H&E), toluidine blue and fast red, Masson's trichrome stain and others. All sponges exhibited similar cell distribution, with live cells present throughout all layers of the sponge.

Figure 1B:
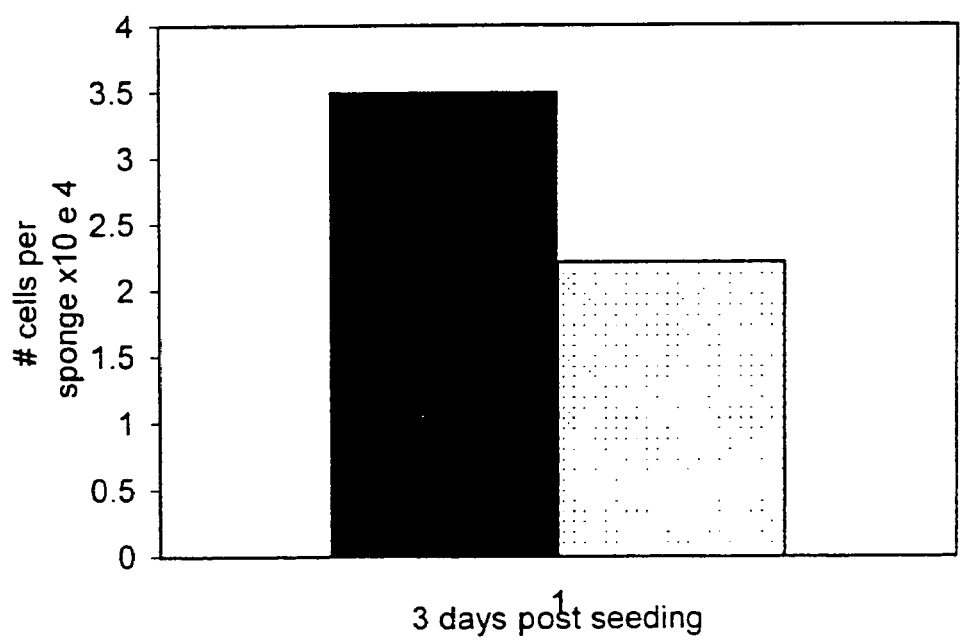
FIG. 1B shows human chondrocyte viability on a matrix substantially devoid of plasminogen compared to a standard sponge comprising an exogenous anti-fibrinolytic agent.
Figure 1C:
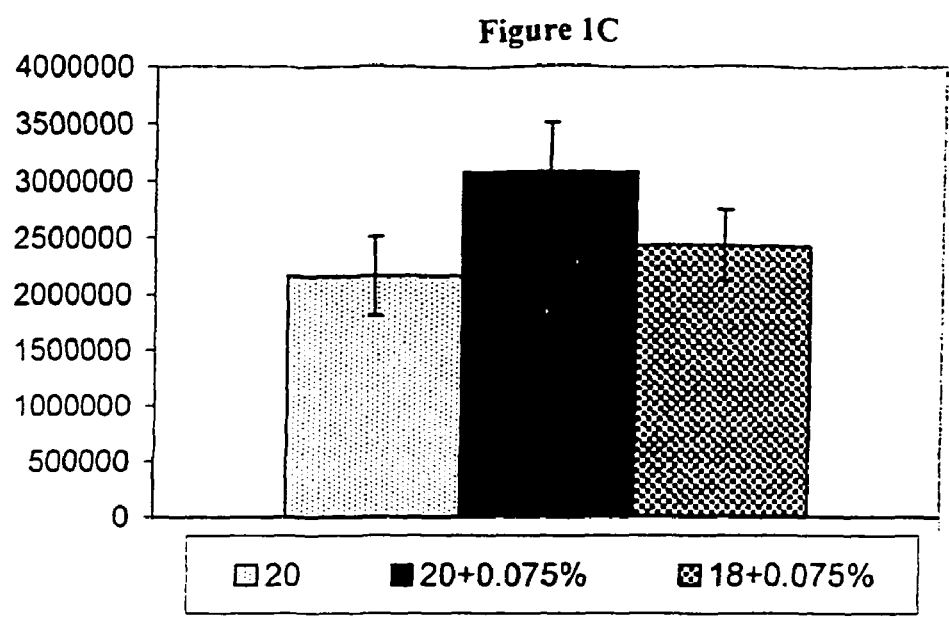
FIG. 1C shows the viability of human chondrocytes seeded on matrices substantially devoid of plasminogen, with or without hyaluronic acid.
Figure 1D:
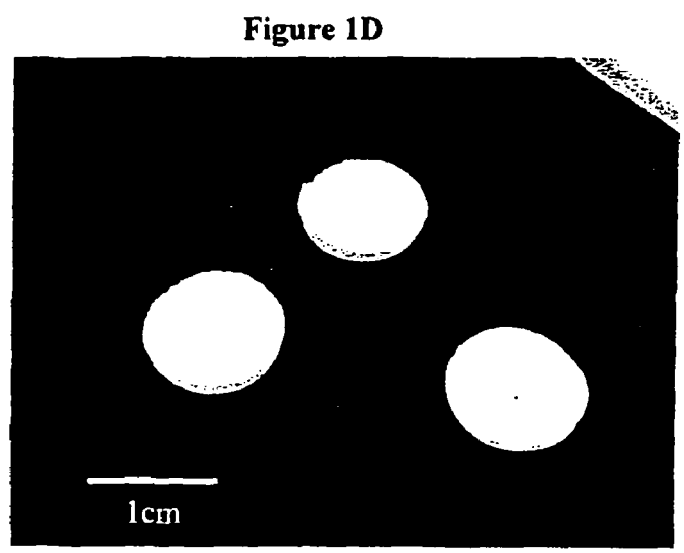
FIGS. 1D and 1E show pictures of the matrices of the invention, dry and seeded with cells, respectively.
Figure 1E:
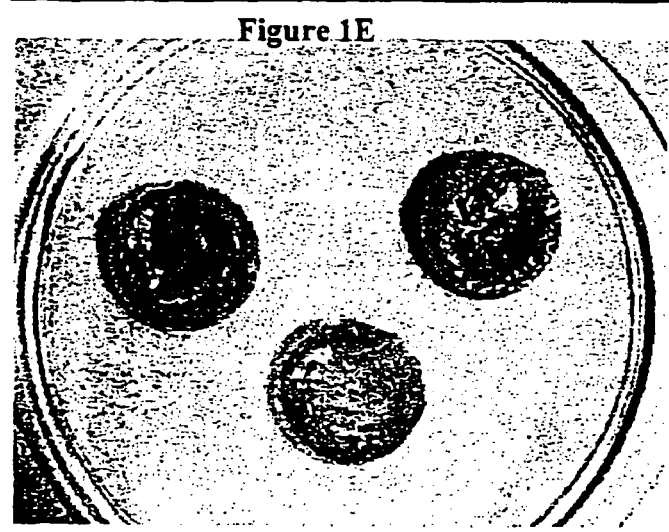

Examples of cell growth in the fibrin sponge of the invention are shown in FIGS. 1A and 1B and FIG. 2. Each sponge was seeded with $5 \times 10^6$ porcine or human chondrocytes in 30 microliter volume, allowed to incubate one hour and fresh media was added. After three days the sponges were degraded in collagenase and the number of live cells was counted after staining with trypan blue. FIG. 1A shows the increased viability of porcine chondrocytes following a three day incubation seeded on matrices with (speckled) and without plasminogen (solid). After three days, more than 50% of the cells remained viable as compared to about 20% of the cells seeded on the standard matrix prepared from plasma proteins comprising tranexamic acid. FIG. 1B shows the viability of human chondrocytes seeded on matrices with (speckled) and without plasminogen (solid-dry) following a three-day incubation. The plasminogen free sponges showed superior cell viability when seeded with human chondrocytes when compared to the sponges comprising tranexamic acid. FIG. 1C shows cell viability after three days on three different sponge compositions. All sponges comprised plasma proteins substantially devoid of plasminogen and were seeded with about $4 \times 10^6$ human chondrocytes. The speckled bar represents viability on a 20 mg plasma protein/ml sponge, without additive present. The solid black bar represents cell viability on a sponge comprising 20 mg/ml and 0.075% hyaluronic acid. The checkered bar represents cell viability on a sponge comprising 18 mg/ml and 0.75% hyaluronic acid. It can be seen that all three sponges provide a good scaffold for cell seeding. FIGS. 1D and 1E show photographs of one centimeter (1 cm) diameter dry sponges and as cell-bearing implants, respectively.

Figure 2A:
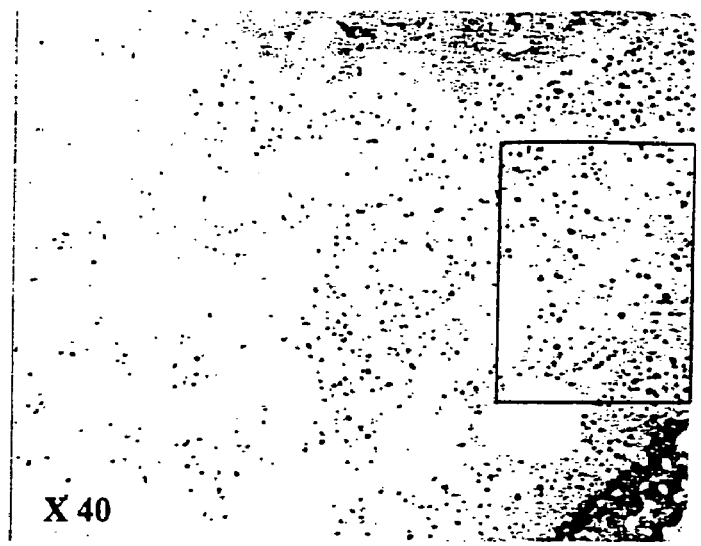
FIGS. 2A-2C show histological sections of chondrocyte distribution in the fibrin sponges substantially devoid of plasminogen, following one-week culture.
Figure 2B:
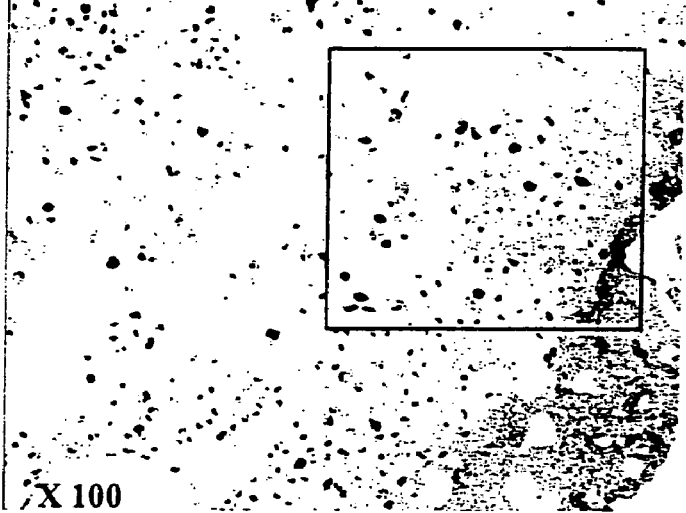
Figure 2C:
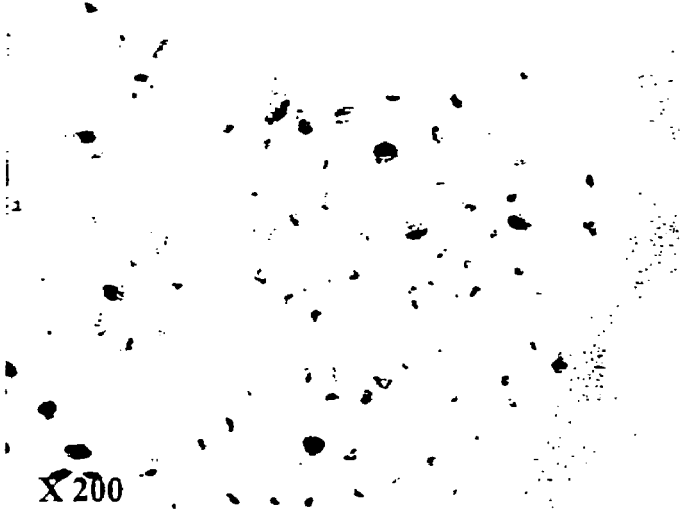

FIG. 2A-2C show histological cross sections through the center of a matrix comprising human chondrocytes following 1-week incubation. The fibrin sponge was made of commercial fibrinogen substantially devoid of plasminogen (Omrix, 20 mg/ml) comprising 0.05% hyaluronic acid and $1 \times 10^6$ human cells. Note the infiltration of the chondrocytes into the sponge. FIGS. 2A, 2B and 2C show 40×, 100× and 400× magnifications, respectively.

Example 7 in vitro Degradation Assay

The assay was carried out to determine the rate of degradation of the sponge of the invention. Differences in the degradation rate can be seen between the sponge of the invention and a standard sponge comprising fibrinogen and an exogenous anti-fibrinolytic such as tranexamic acid.

The assay was performed in the following manner: three different types of sponges were prepared, each having the same fibrinogen concentration, the same thrombin concentration (1.5U/mg protein) and the same hyaluronic acid concentration. The differences were the source of fibrinogen and hyaluronic acid.

A fibrin sponge comprising 10% tranexamic acid, fibrinogen (Omrix, 27 mg/ml), crosslinked hyaluronic acid (Syvisc, 0.08%).

A fibrin sponge prepared from fibrinogen substantially devoid of plasminogen (Omrix, 27 mg/ml) crosslinked hyaluronic acid (Synvisc, 0.08%).

A Fibrin sponge prepared from fibrinogen substantially devoid of plasminogen (Omrix, 27 mg/ml) non-crosslinked hyaluronic acid (BTG, 0.08%).

The experiment was performed as follows: Five sponges prepared in 96 well plates were placed in 48 well plates and 750 ul of 10M urea was added to cover the sponges.

Figure 3A:
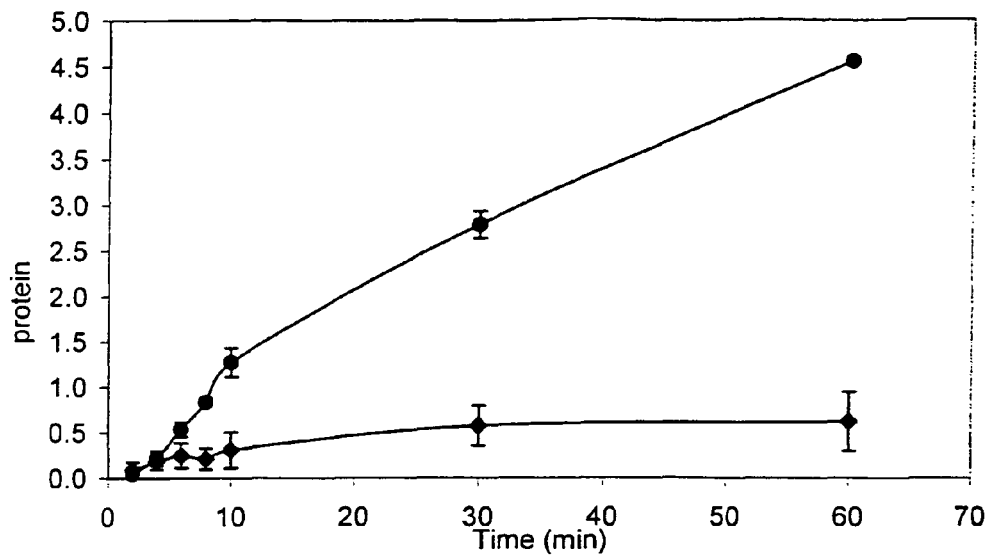
FIGS. 3A and 3B show the rate of degradation of the sponge substantially devoid of plasminogen compared to a sponge comprising tranexamic acid, in urea or collagenase.

Samples of 20 ul were collected from each well at the following points: 1, 2, 3, 4, 5, 8 minutes, 10 minutes, 30 minutes, 1 hrs. Protein from each sample was measured in a standard Bradford assay. The results are presented in FIG. 3A.

The sponge (•) comprising standard fibrinogen and 10% tranexamic acid underwent rapid degradation as measured by protein (mg/ml) detected in the supernatant and could not be seen after 10 minutes, whereas the sponge comprising the plasma proteins substantially devoid of plasminogen remained stable.

Figure 3B:
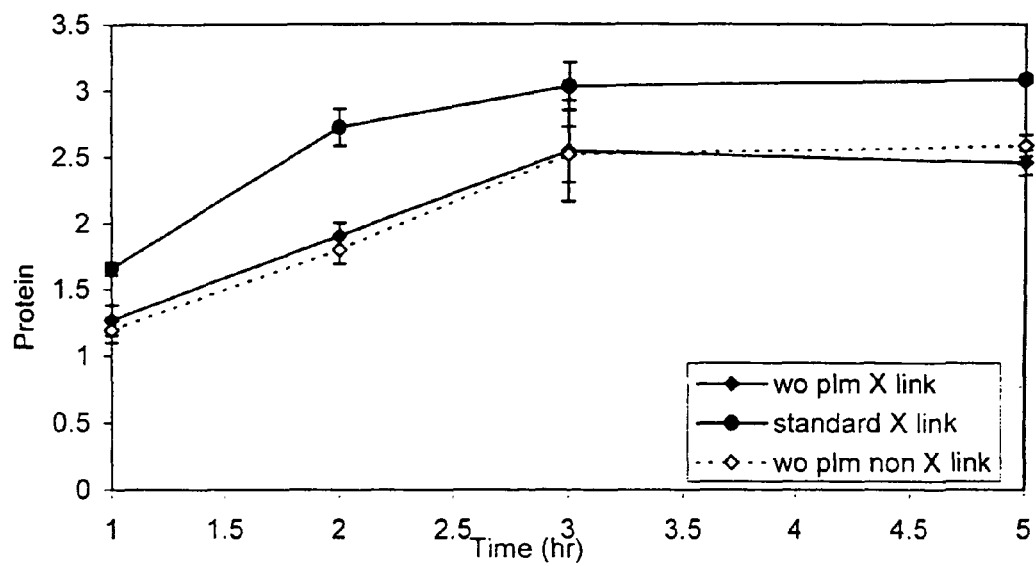

In a similar experiment, the sponges were degraded with collagenase. The test sponges were incubated in 400 μl of collagenase (1.7 mg/ml) diluted 1:10 in DMEM without FBS at 37° C. until completely dissolved. At different time points, samples were collected and examined for protein concentration by Bradford assay. The results are presented in FIG. 3B. The sponge comprising 10% tranexamic acid and cross linked hyaluronic acid (X link) degraded much faster than the sponges comprising the fibrinogen substantially devoid of plasminogen (wo plm) comprising either cross linked or non-cross linked hyaluronic acid (wo plm x link, wo plm non x link, respectively)

Example 8

Release of Bioactive Agents from the Matrix

For certain applications, sustained release of a bioactive agent such as a growth factor may be desirable. The incorporation and release of growth factors from the matrix of the invention was assessed in vitro and may be assessed in vivo using radiolabeled or tagged growth factors, for example fluorescent-labeled, alkaline phosphatase labeled or horseradish peroxidase-labeled growth factor. The fraction and rate of released agent is measured by following the radioactivity, fluorescence, enzymatic activity or other attributes of the tag. Similarly, release of enzymes from the matrix is determined by analyzing enzymatic activity into the microenvironment in an in vitro or in vivo assay. Specifically, the release of an FGF from the matrix of the invention was performed as described herein.

The rate of growth factor release was determined from sponges prepared in two alternate methods. In one instance FGF2 was adsorbed to heparin and the combined product was added to the plasma protein solution. In the second instance, each component was added separately to the individual solutions: heparin was added to the plasma protein solution while FGF2 was added to the thrombin solution. Sponges were cast from both mixtures and FGF2 release was determined in an FDCP (Factor Dependent Cell-Paterson) assay, vide supra.

Materials and methods:

Plasma proteins (approximately 20-65 fibrinogen mg/ml; Omrix, plasminogen-free).

Non-cross linked hyaluronic acid (MTF or BTG),

Heparin (Sigma, MW 6,000)

FGF2 (ProChon) 2.5 ug per 75 ul sponge

Fibrin sponges substantially devoid of plasminogen and of organic chelating agents were prepared using the method described in Example 1 with the following modification: the plasma protein solution comprised non-crosslinked hyaluronic acid to a final concentration of 0.08%.

The first set of sponges was prepared by mixing heparin solutions with FGF2 and adding the mixture to the plasma protein solution.

The second set of sponges was prepared by adding heparin to the plasma protein solution to a final concentration of 0.1, 0.5 or 2.5 ug/ml. FGF2 was added to the thrombin solution to bring the final concentration to 2.5 ug/sponge. The sponges were cast as described above. FGF2 release was determined in a FDCP assay as described below.

FDCP Assay: The FDCP cell line is a murine immortalized, interleukin 3-dependent cell line of myelocytic bone marrow origin that does not express endogenous FGF Receptors (FGFR). Upon transfection with FGFR cDNA, the FDCP cell line exhibited a dose-dependent proliferative response to FGF that can replace the dependence on IL-3. FGFR transfected FDCP cells can therefore been used to screen for FGFR signaling. FDCP cells response to various ligands is quantitated by a cell proliferation assay with XTT reagent (Cell Proliferation Kit, Biological Industries Co.). The method is based on the capability of mitochondrial enzymes to reduce tetrazolium salts into a colorigenic compound, which can be quantitated and is indicative of cell viability. Specifically, FDCP cells stably expressing the FGFR1 (FDCP-FGFR1) were grown in "full medium" (Iscove's Medium containing 2 ml glutamine, 10% FCS, 100 ug/ml penicillin, ML/ml streptomycin) supplemented with 5 ug/ml heparin. Cells were split every 3 days and kept in culture no more than one month. One day prior to the experiment the cells were split. Before the experiment the cells were washed 3 times (1000 rpm, 6 min) with full medium. The cells were resuspended and counted with Trypan Blue. Twenty thousand ($2\times10^4$) cells were added to each well of 96-well plate in 50 μl full medium with or without heparin. Conditioned medium from the sponges containing FGF or FGF complexed with the various glycosaminoglycans was added in an additional volume of 50 μl full medium to bring the final volume to 100 μl. The plate was incubated for 48 hours at 37° C. To test cell proliferation, 100 μl of PMS reagent was added to 5 ml of XTT reagent and mixed well (according to manufacture protocol). 50 μl of the latter solution were aliquoted into each well, and the plates incubated at 37° C. for 4 hours and the color developed was read by a spectro-ELISA reader at $A_{490\ nm}$.

Figure 4A:
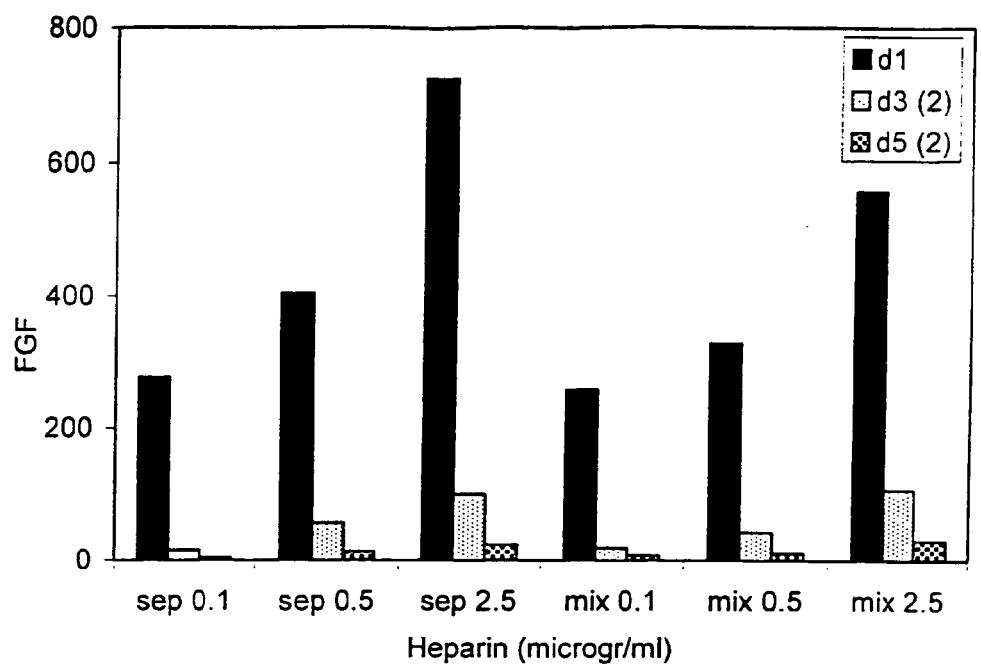
FIGS. 4A-4B represent FGF release from fibrin matrices substantially devoid of plasminogen comprising 0.08% crosslinked hyaluronic acid and varying amounts of heparin prepared in two different ways.
Figure 4B:
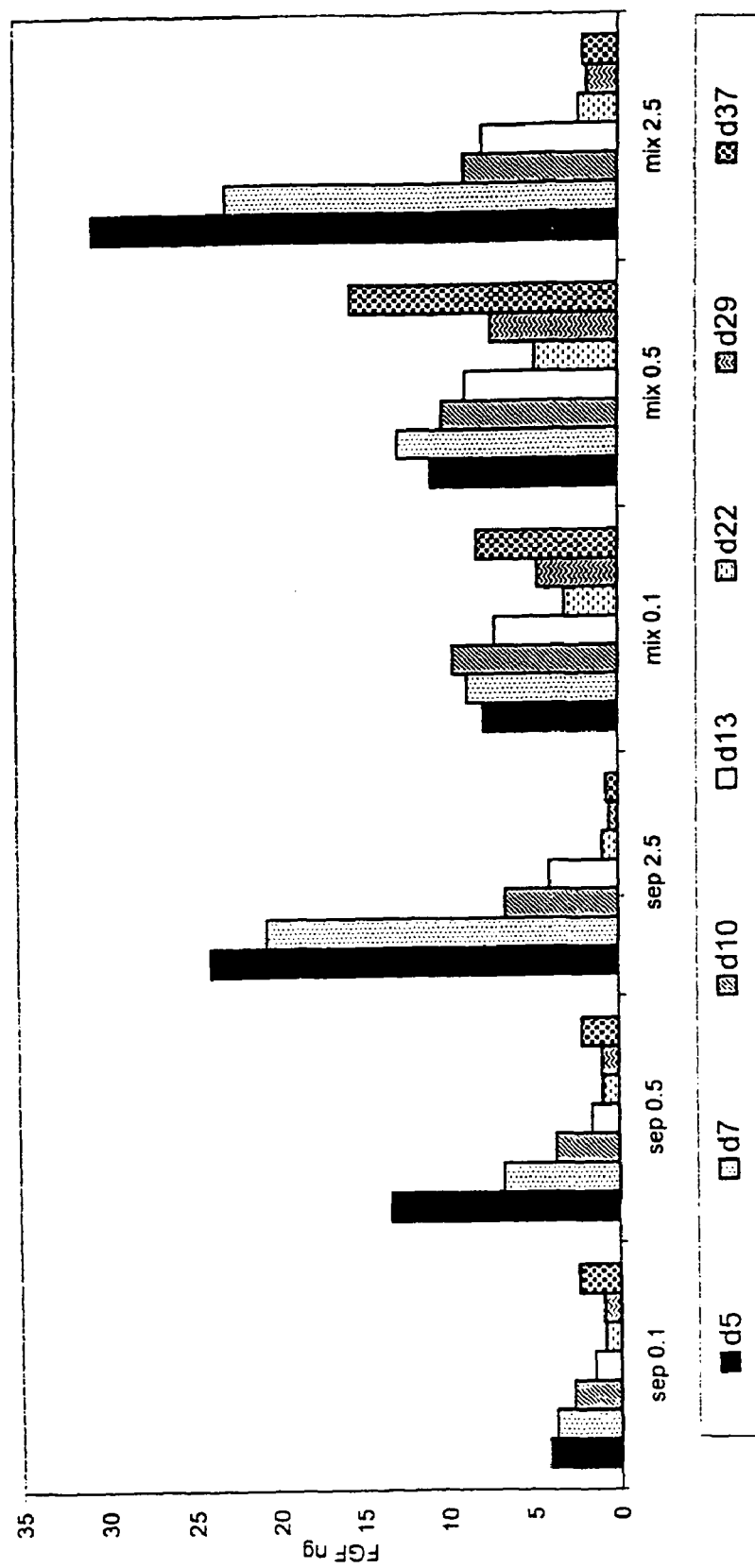

FIGS. 4A and 4B show the results of this assay for a sponge of the invention made of commercial plasma proteins substantially devoid of plasminogen (Omrix, final 20 mg/ml) comprising 0.08% non-crosslinked hyaluronic acid, either by adding heparin and FGF2 variant that have been premixed (mix) to the plasma protein component of the sponge ab initio or by adding the heparin to the plasma protein solution and the FGF2 variant to the thrombin solution (sep), followed by mixing and casting the clot. The sponges comprised either 0.5, 1.5 or 2.5 ug/ml heparin and 1 ug total FGF2 variant. Supernatant was tested after various days and results for proliferation recorded. FIG. 4A shows the release of FGF2 variant from a sponge comprising both heparin and FGF2v after 1, 3 and 5 days. FIG. 4B shows the percent of total release after 5-37 days. The release profile of FGF is dependent on the concentration of heparin in the sponge. Without wishing to be bound to a particular theory, the heparin may serve to stabilize the released FGF.

Figure 4C:
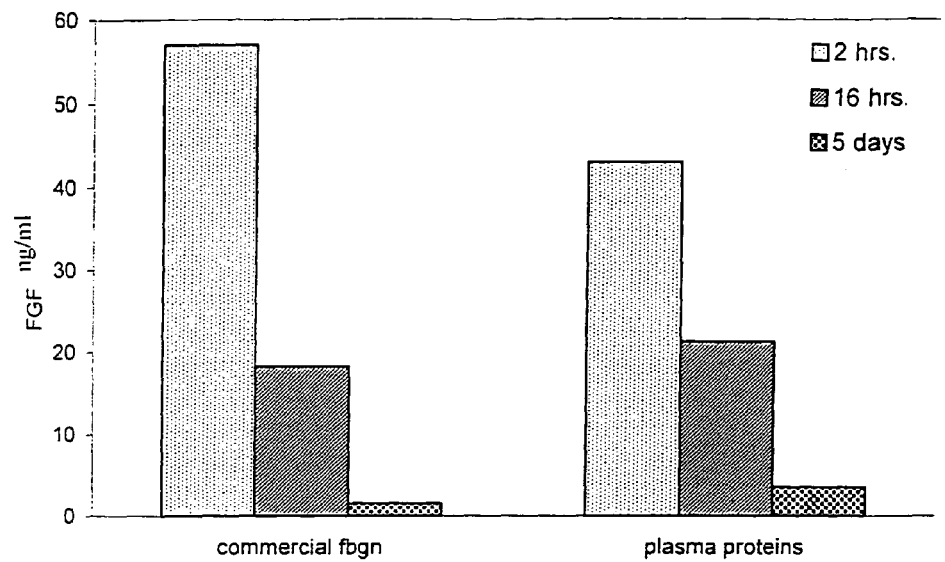
FIG. 4C shows a bar graph of FGF release from plasma protein matrices comprising tranexamic acid (commercial) or human plasma protein matrix comprising partially purified plasma proteins and 0.024% hyaluronic acid and FGF and heparin incorporated, ab initio.
Figure 4D:
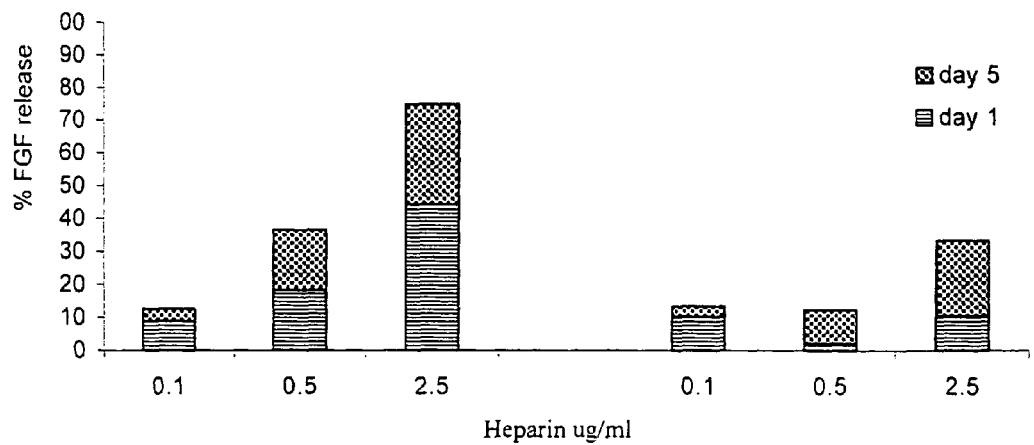
FIG. 4D shows the FGF release pattern from plasma protein matrices substantially devoid of exogenous anti-fibrinolytic agents comprising varying concentrations of thrombin and heparin.

FIG. 4C shows the release profile over 5 days of an FGF variant from a sponge comprising heparin and either commercial fibrinogen and tranexamic acid or plasma proteins, substantially devoid of antifibrinolytic agents. The results show a good release profile for both compositions.

Example 9

Chondrocyte Isolation and Culturing

Reagents:
Collagenase Type 2; Worthington Biochemical Corp. (Cat. #: 4147)
Stock solution: 1700 units/ml in medium (in MEM)
Minimal Essential Medium (MEM) Gibco BRL (cat: 21090-022)
Fetal Bovine Serum (FBS); Gibco BRL (cat: 16000-044)
L-Glutamine Solution; Gibco BRL (cat: 25030-024)
Complete medium: Minimal Essential Medium (MEM) supplemented with 10% fetal calf serum (FCS), 2 mM L-Glutamine and 100 U/ml penicillin, and 100 μg/ml streptomycin
Preparation of Implants for Articular Cartilage The sponge of the present invention may be used as a cell bearing scaffold for tissue repair and regeneration. In one aspect, the cells are cultured on the sponge in vitro, prior to implantation. In another aspect, the sponge is seeded with cells immediately before implantation and the cells allowed to proliferate in vivo.

Cartilage biopsies from fresh pig cartilage were sectioned into small pieces, approximately of 3-4 mm thick, washed aseptically with PBS and placed in a new tube containing 3 ml MEM medium. The cartilage may be obtained from any vertebrate species, and is preferably allogeneic or autologous.

Collagenase type II was diluted 1:5 and 1 ml was added to the cartilage pieces and the mixture was shaken gently in a 37° C. incubator over night. When most of the sample was digested the suspension was poured through sterile gauze to remove matrix debris and undigested material. The filtrate was centrifuged and washed twice to remove residual enzyme.

The number of cells was determined by a hemocytometer and viability was determined by Trypan blue exclusion. The cells were plated in 150 $cm^2$ tissue culture flasks in 30 ml of culture medium at a concentration of $5\times10^6$ cells/ml. Flasks were placed in a 37° C. incubator at 5% $CO_2$ atmosphere and 95% humidity. The culture medium was changed every three to four days. The cells adhere and become confluent following one week incubation.

At confluence, the cell medium was removed and 3 ml of a trypsin-EDTA solution were added. Thirty ml MEM+FBS was added, the solution was centrifuged at 800 g for 10 minutes. The supernatant was removed, the pellet dispersed and the cells were counted. To create a cell-bearing matrix, $10^2$-$10^6$ cells were seeded on a fibrin scaffold of 9 mm in diameter and a thickness of 2 mm (approximately 0.2 $cm^3$). The matrices were placed in a 37° C. incubator for 1 hour and 1 ml of fresh medium was added to each. The medium was replaced with fresh medium and every few days the matrices were taken to cell proliferation and differentiation analysis.

Furthermore, the cell population grown on the above matrices expresses several of the chondrocyte differentiation markers. One of several phenotypes expressed during chondrocyte differentiation is glycosaminoglycan (GAG) production. The presence of GAGs may be identified in histological staining using Alcian blue and quantitated using the DMB (3,3'-dimethoxybenzidine dihydrochloride) Dye method. Cartilage extracellular matrix may also be identified by staining with toluidine blue and fast red.

Example 10

Cell Proliferation Assay

Proliferation of the cartilage cells on the matrix of the invention was quantitated by one of two methods, CyQUANT® (Molecular Probes) or XTT reagent (Biological Industries, Co.). The fibrin matrix was dissolved in collagenase or other enzymes and the cells collected by centrifugation and subjected to analysis according to manufacturer's protocols.

In one experiment, human articular chondrocytes ($10^4$-$10^6$ cells/30-100 ul) were grown on matrices substantially devoid of exogenous anti-fibrinolytic agents in microwell plates. The cells were grown overnight in MEM, 34 U collagenase was added and the cells or cells within sponge incubated for four hours. XTT reagent was added for 3-4 hours and the plates were read in an ELISA reader at A490 mm. The results show that the proliferation rate of the cells was not impaired by the presence of the sponge nor by the addition of the collagenase.

FIGS. 5A-5D show porcine chondrocytes ($0.5\times10^6$ cells in 30 ul) that have been cultured (6 days) on a fibrin sponge made from pooled human plasma (30 mg/ml) comprising 0.024% Hylan and 1 ug FGF variant. FIGS. 5A and 5B show hematoxylin and eosin (H&E) staining (×100 magnification). FIG. 5C shows a 400× magnification of a sponge section stained with Masson's stain. Note the staining for cells and intracellular matrix surrounding the cells. FIG. 5D shows a ×200 magnification section of sponge stained with Masson's stain. Note the cells present within many of the pores.

Example 11

Seeding and Growth of Cells and Cell Lines on the Fibrin Matrix

In order to determine the capacity of the plasma protein matrix to support cell growth several different cell types and cell lines were seeded and allowed to grow. Specifically, a primary rat liver hepatocytes were cultured on the matrix. One cm diameter sponges comprising plasma proteins substantially devoid of plasminogen (20 mg protein/ml, Omrix), 0.075% hyaluronic acid and 1 IU thrombin/ml were prepared.

Figure 6A:
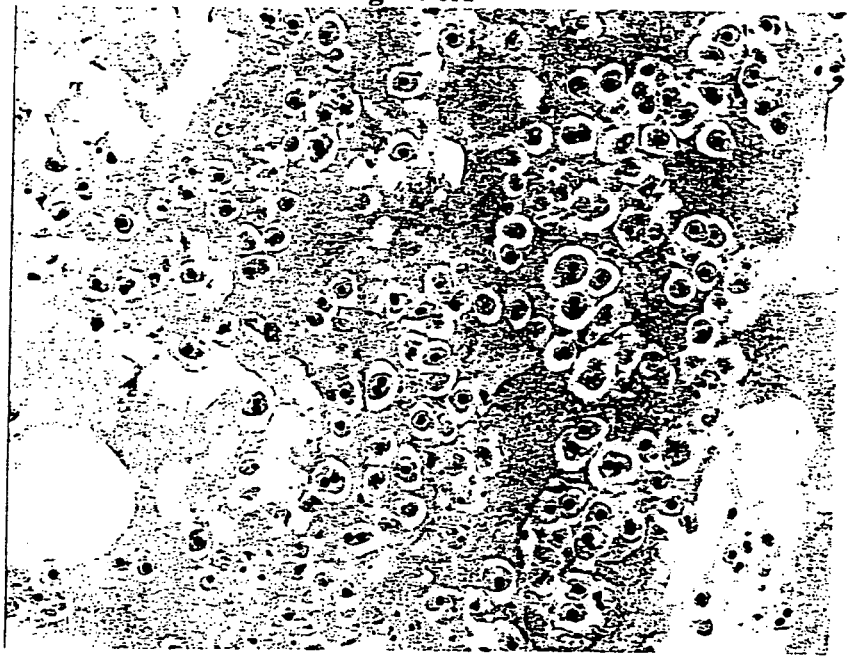
FIG. 6A shows primary rat hepatocyte cells incubated for three days on a porous freeze-dried plasma protein matrix, substantially devoid of plasminogen.

Approximately 6.6×10⁵ primary hepatocytes were seeded on the sponges in HDM (hormonally defined medium) without serum and allowed to incubate for three days at which histological samples were made and stained with H&E. FIG. 6A shows a representative section of a sponge comprising the hepatocytes. Note the good dispersion of the cells throughout the matrix and the presence of typical cells maintaining their hepatic characteristics.

Figure 6B:
FIGS. 6B and 6C show the CHO and L8 cell lines incubated for three days on a porous freeze-dried plasma protein matrix, substantially devoid of plasminogen.
Figure 6C:

Two cell lines were tested for viability and growth within the sponges, the L8 rat skeletal muscle cell line and the CHO Chinese hamster ovary cell line. Two million cells were seeded on each matrix and allowed to incubate for three days. The CHO cell line was cultured in Iscove's medium, the L8 line was cultures in DMEM. Histological sections were made and stained with H&E. FIGS. 6B and 6C show sponge sections with the CHO and L8 cells, respectively. In addition, the CHO and L8 cells were removed from several of the sponges and counted using Trypan blue. The L8 cells exhibited 57-67% viability while the CHO cells exhibited more than 85% viability. Both figures show good cell distribution and cell viability. The matrix of the invention provides a superior scaffold for tissue engineering and regeneration.

Example 12

Ectopic Cartilage Formation in Nude Mice

The assay was designed to determine the ability of isolated chondrocytes to create neocartilage in an ectopic site, and to determine the quality of this cartilage compared to natural cartilage.

Human and porcine chondrocytes seeded on a matrices of the invention were used to induce ectopic cartilage on the backs of nude mice Treatment arms: The study groups included different amounts of cells seeded onto the fibrin matrix substantially devoid of plasminogen. Either 10e5 (10^5) or 10e6 (10^6) human or porcine chondrocytes were seeded onto a fibrin sponge from a 96 well plate (~65 ul). The control group consisted of matrices implanted without cells.

Preparation of fibrin matrices: The method for sponge preparation consists of mixing a plasminogen free fibrinogen solution (Omrix), with a thrombin solution (Omrix) in the presence of non-crosslinked hyaluronic acid (BTG), resulting in final concentration of 20 mg fibrinogen/ml, 0.5 IU thrombin/mg fibrinogen and 0.08% hyaluronic acid. The solutions were added to a mold (96 well plate, volume of 65 μl) where clotting took place at room temperature. The clot was rapidly frozen at −70° C. followed by lyophilization resulting in an implant (matrix, sponge) having a spongy texture.

Seeding: Sponges were seeded with human or porcine chondrocytes ($10^5$-$10^6$/20 ul culture medium in a 96 well plate and incubated at 37° C. for 1 hour. Culture medium was added to the well and the sponge incubated 24-48 hours. The sponge was placed into subcutaneous incisions made on the back of nude mice.

Implantation procedure: Animals were anesthetized using ketamine-xylazine. Back skin was shaven and cleaned using alcohol. Two incisions, were made on each side of the back, parallel to the spine. A subcutaneous pocket or a pocket in the muscle fascia was made from each incision using blunt dissection. The sponges were implanted in the pockets according to treatment arms. The skin was closed with single suture. Each treatment was repeated 5 times and each mouse was implanted with 4 sponges. See Table 2 hereinbelow.

TABLE 2

Experimental Setup

| Mouse No. | Left proximal | Left distal | Right proximal | Right distal | Tagging |
|---|---|---|---|---|---|
| 1 | 1 × 10^5 Human | 1 × 10^6 Human | 1 × 10^5 Porcine | 1 × 10^6 Porcine | No tag |
| 2 | 1 × 10^6 Human | 1 × 10^5 Human | 1 × 10^6 Porcine | Sponge w/o cells | 1 Rt ear |
| 3 | 1 × 10^6 Porcine | 1 × 10^5 Porcine | 1 × 10^5 Human | 1 × 10^6 Human | 1 Lt ear |
| 4 | 1 × 10^6 Porcine | Sponge w/o cells | 1 × 10^6 Human | 1 × 10^5 Human | 2 Rt ear |
| 5 | 1 × 10^6 Human | 1 × 10^6 Porcine | Sponge w/o cells | 1 × 10^5 Human | 2 Lt ear |
| 6 | Sponge w/o cells | Sponge w/o cells | 1 × 10^6 Porcine | 1 × 10^5 Porcine | RT + LT |

Induced cartilage formation evaluation: One or four weeks post implantation the mice were sacrificed and the implants with their surrounding tissue retrieved and prepared for histology evaluation. The microscopically assessment consists of a complete morphological description of the implant. Additional analysis include H&E staining safranin O, alcian blue and anti-collagen type II staining.

Figure 7A:
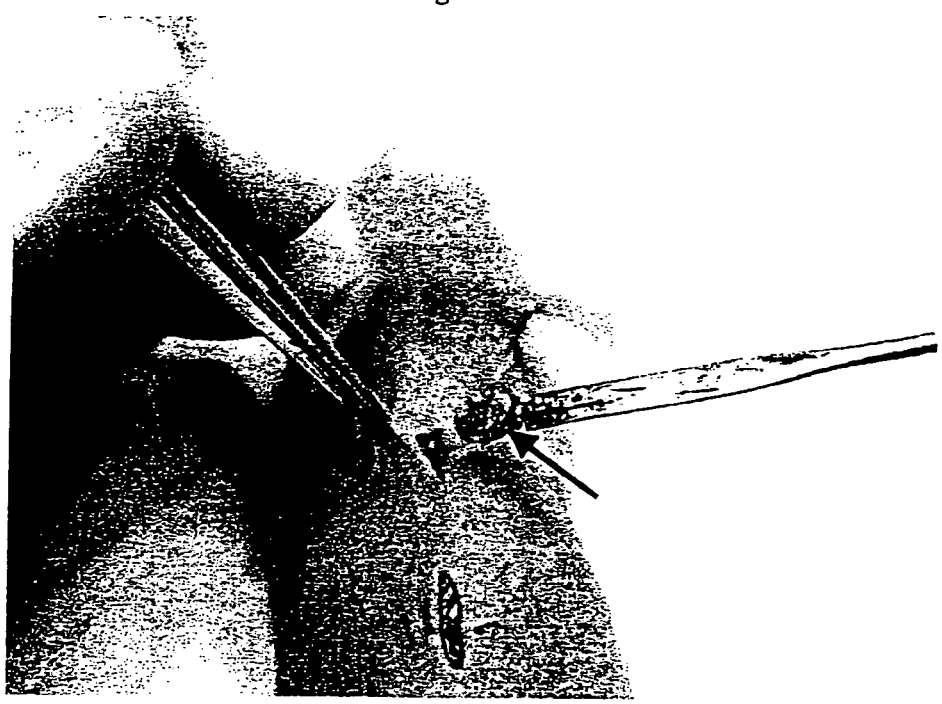
FIG. 7A shows the insertion of a cell-bearing porous freeze-dried plasma protein matrix, substantially devoid of plasminogen into a subcutaneous pocket of a nude mouse.
Figure 7B:
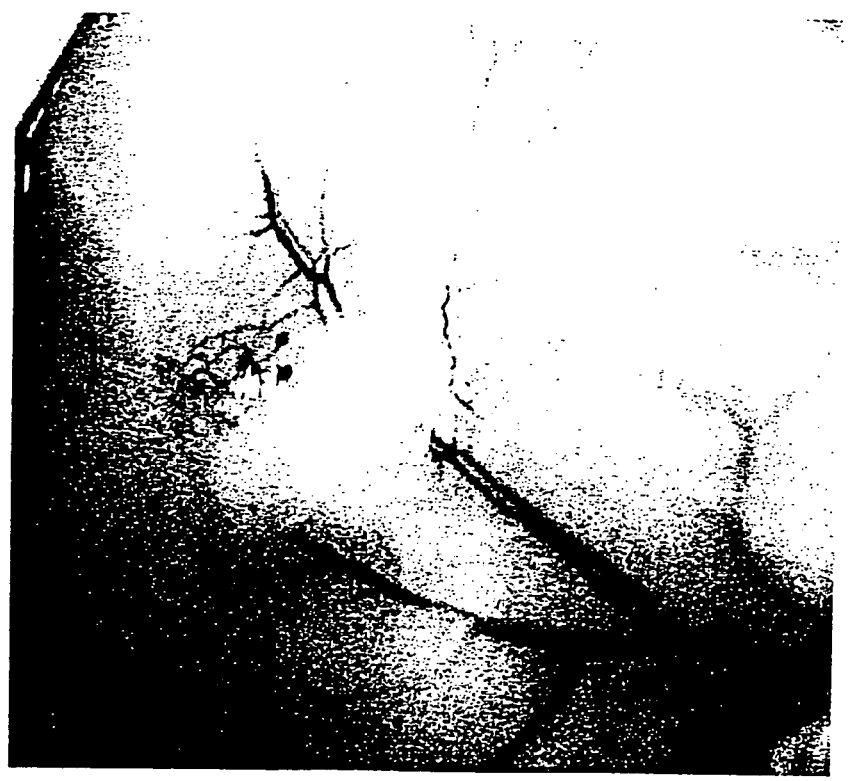
FIG. 7B shows the neocartilage that developed.
Figure 8A:
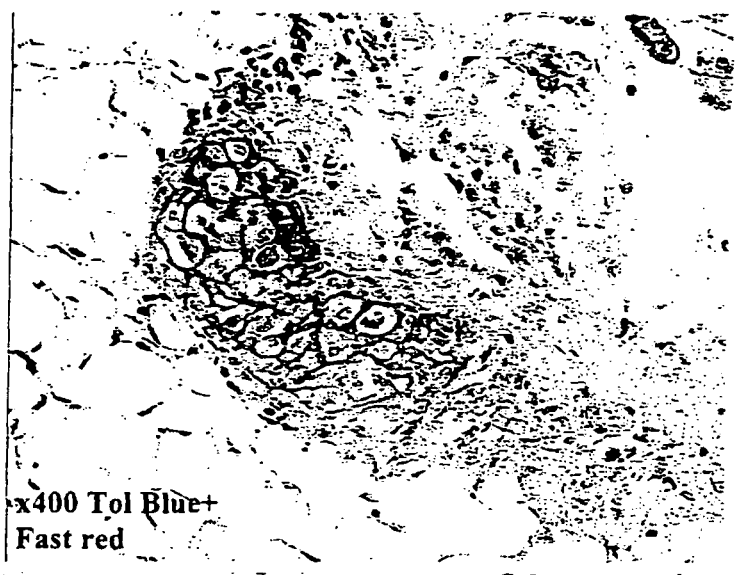
FIGS. 8A-8C show histological cross sections of a neocartilage nodule.
Figure 8B:
Figure 8C:
Figure 9A:
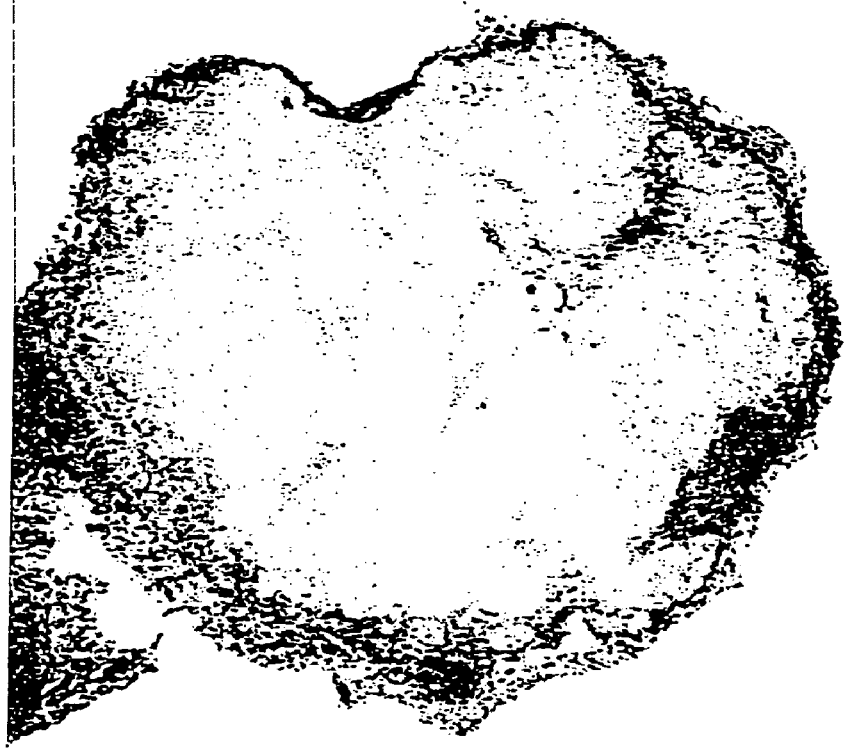
FIGS. 9A-9B show histological cross sections of the neocartilage nodule stained with H&E, at 10× and ×100 magnification.
Figure 9B:

FIG. 7A shows the implantation procedure. FIG. 7B shows the growth of ectopic cartilage derived from a cell embedded sponge ($10^5$ cells) on the back of a mouse, FIGS. 8A, 8B and 8C show a hematoxylin-eosin stained section of human chondrocytes of a neocartilage plug after one week. FIG. 8A shows a histological section with many cells exhibiting strong staining of cartilage matrix using toluidine blue and fast red. FIGS. 8B and 8C show histological sections stained with H&E. Note the good cell dispersion and the presence of cell matrix surrounding the cells. FIGS. 9A and 9B show a hematoxylin-eosin stained section of porcine chondrocytes at 40× and 200× magnification, after 4 weeks growth in situ.

The results of this experiment confirmed that the matrix comprising plasma proteins substantially devoid of plasminogen is an effective matrix for the formation of cartilage. The matrices are non-immunogenic, non-toxic and support chondrocyte growth and differentiation.

Example 13

Method of Matrix Preparation

Figure 10A:
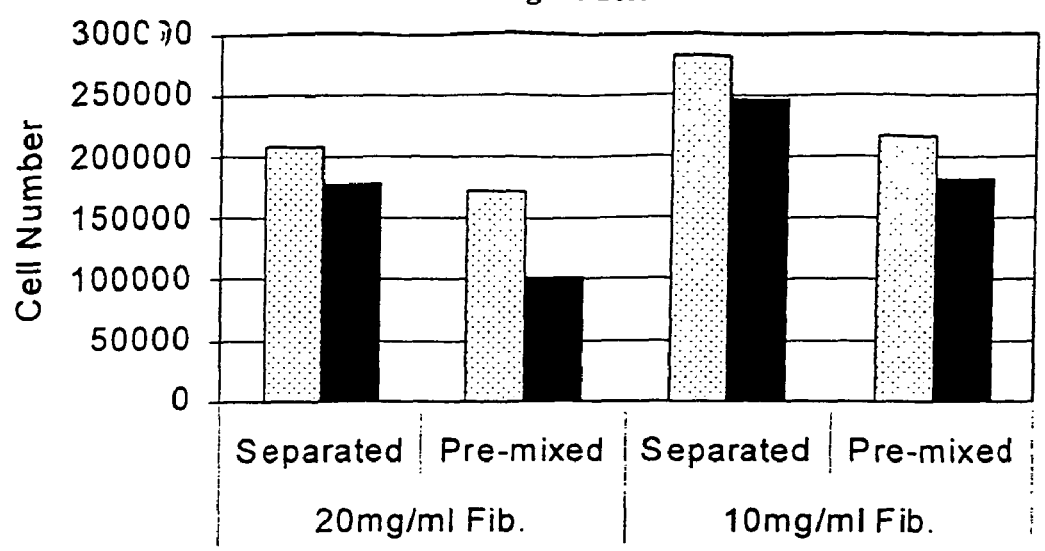
FIG. 10A depicts cell viability on plasma protein sponges prepared either by premixing the plasma protein and thrombin solutions or by mixing the solutions during casting.
Figure 10B:
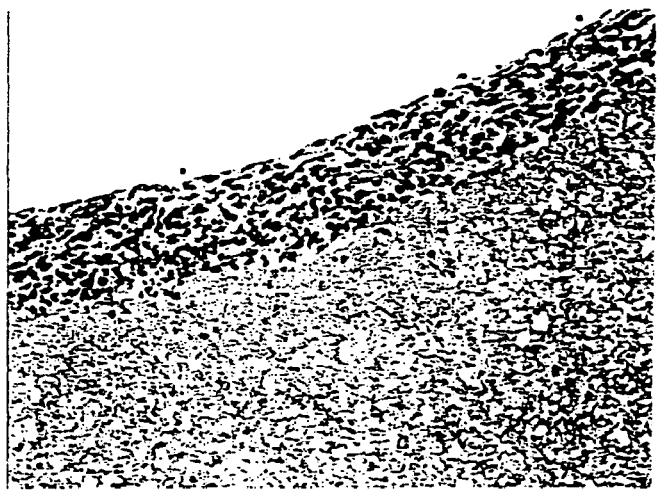
FIGS. 10B and 10C show histological cross sections of cell-bearing sponges substantially devoid of plasminogen prepared by premixing the plasma protein and thrombin solutions (10B) or by mixing the plasma protein and thrombin solutions during the casting step (10C).
Figure 10C:

Sponges were prepared in two different ways and tested for cell viability and cell dispersion. Both methods comprise the steps of preparing the plasma protein and thrombin solutions. One method further comprises sequential dispensing of the thrombin and fibrinogen solutions into a mold. The second method, "premixing", requires that the two solutions be mixed prior to casting into a mold. The resulting sponges are different in terms of their porosity and cell absorption capabilities. FIG. 10A shows chondrocyte cell viability on the sponges prepared using the two different methods. Cell viability is similar on both types of sponges. A difference can be seen in porosity and cell dispersion. FIG. 10B shows cells sitting on the upper layers of a sponge prepared using the premixing method. FIG. 10C shows cell distribution throughout the matrix in a sponge prepared according to the method where the solutions are cast into the mold sequentially. Certain applications may benefit one type of sponge over another.

Example 14

Sheep Model of Cartilage Repair

This study was designed to evaluate the capacity of the chondrocyte embedded fibrin matrix of the invention to repair cartilage in a large animal model. A total of 20 sheep each weighing about 60-80 kg were chosen. Eight of the animals underwent a chondrocyte harvesting procedure prior to implantation. The harvested chondrocytes were expanded and seeded onto recombinant human fibrin matrices.

Animal housing conditions conformed to applicable laws and regulations relating to laboratory animals. The experiments were performed in accordance with the principles of the local laws for Animal Experiments. The animals were examined for evidence of disease or lameness. Acceptability into the study was contingent on being disease free, clinically sound, and no history of prior use. Osteoarthritis was excluded by a preoperative X-ray. The animals were conditioned for an appropriate period of time as determined by the institution. A unique number tattoo and ear tag identified each animal. Animals were assigned to the treatment groups by random allocation of identification numbers. The study design is shown below in table 3:

TABLE 3

| # Sheep | Treatment | Type of matrix |
|---|---|---|
| 1A–7A | untreated | untreated |
| 1B–7B | microfracture | microfracture |
| 1C–4C | Matrix alone | TEA + X-linked HA |
| 5C–8C | Matrix alone | Plasminogen free + X-linked HA |
| 9C–12C | Matrix alone | Plasminogen free + non X-linked HA |
| 1D–4D | Matrix + cells | Plasminogen free + X-linked HA |
| 5D–8D | Matrix + cells | Plasminogen free + non X-linked HA |

Animals were observed daily for general health throughout the course of the study. In the unlikely event that an animal will become injured, ill, or moribund, care will be conducted in accordance with current veterinary medical practice. If warranted for humane reasons, euthanasia will be conducted in a humane manner according to the guidelines set forth by the AVMA (American Veterinary Medical Association) Panel on Euthanasia (JAVMA, March 2000). The attending veterinarian will perform a clinical diagnosis and treatment on the animal if it shows signs of illness.

Bodyweight measurements were taken from all animals once during the quarantine period, prior to surgery (Day 0) and at the end of the study (Day 112).

Group A. Untreated defects: In 7b animals (14 defects) the chondral defects were created in the condyle and were left untreated.

Group B. Microfracture: In 7 animals (14 defects) microfracture was performed in without further treatment. Four microfractures were performed with special awls in each defect until punctuate bleeding was observed.

Group C Fibrin matrix alone: Fibrin matrices comprising TEA and cross linked hyaluronic acid (X-linked HA) were implanted in 4 sheep (1C-4C). A fibrin matrix prepared from the plasminogen free fibrinogen and either X-linked (5C-8C) or non-x-linked HA (9C-12C) were implanted in 4 sheep, each. The matrices were implanted after creating the defects as described below.

Group D Cell bearing fibrin matrix: Fibrin matrices prepared from plasminogen free fibrinogen and either cross linked hyaluronic acid (X-linked HA, 1D-4D)) or non-X-linked HA (5D-8D) were seeded with chondrocytes, and implanted into the knee defects of 4 sheep, each.

Operation: The left knee joint was sterilely draped and opened by an anteromedial approach under general anaesthesia. The medial condyle was exposed, and small pieces of cartilage were harvested from the low weight bearing surfaces of the trochlea and intercondylar notch. The cartilage was cut superficially with a scalpel to avoid bleeding. The wound closure was performed in layers. An external plaster fixation for stifle joint and ankle was applied for five days and cage activity limited to reduce joint loading in order to prevent dislodgement of the patella. The tissue specimen was diced and washed under sterile conditions and the cells isolated by collagenase following a standard digestion protocol. The cells were plated in 75 ml flasks (Coming) and incubated at 37° C. Changing of media was performed every other day. After 3 weeks about 200,000 ($2 \times 10^5$) cells were seeded on the selected fibrin matrices and cultivated for 4 days in 6-well plates. The cell-bearing matrices were sterilely transferred to the operation room. The medial condyle of the right knee of the same sheep was exposed. Using a 4.5-mm punch (Smith & Nephew), two defects, 1 and 2.5 cm distal from the intercondylar notch, were made in the medial condyle of the femur. The defects were outlined with the dermal punch down to the subchondral bone and the cartilage was removed with small curettes. An attempt will be made to remove all of the articular cartilage by gently scraping the calcified cartilage surface. No bleeding should be observed from the subchondral bone. The fibrin matrices were fixed into place using fibrin glue.

After treatment of the defect, bleeding points of the capsule were stopped by cauterization and wound closure performed in layers. The external plaster fixation was applied for another five days and cage activity limited to reduce joint loading in order to prevent dislodgment of the graft and reparative tissue. After removal of the plaster, the sheep were given unrestricted activity in runs, and fed with a balanced nutrition twice a day. Until the second postoperative day 2 g cefazolin was administered thrice daily.

All animals of group C and D were sacrificed at 16 weeks after implantation as described below and in Mankin, H. (NEJM (1974)291:1335-1340).

Necropsy: Animals were humanely sacrificed at 16 weeks postoperatively. Bodyweights were recorded immediately prior to sacrifice. Deep anesthesia was induced with a mixture of ketamine-xylazine and the subject exsanguinated according to the guidelines set forth by the AVMA Panel on Euthanasia (JAVMA, March 2000).

Gross evaluation and sample collection as described in table 4 was performed. The articulating surfaces opposing the defect sites were examined for any abnormal joint surface. Additionally, gross evaluations of the knee joints were made to determine the cartilage repair based on previous scoring criteria listed in Table 5. Femora, patellae, synovium, and popliteal lymph nodes shall be harvested and placed into appropriately labeled containers. Immediately following tissue harvest, gross morphological examination of the cartilage surface was performed and photographic records made of each specimen.

TABLE 4

Gross Evaluation and Sample Collection

| Sample | Gross Evaluation | Sample collection | Photograph and Score |
|---|---|---|---|
| Knee joint (incl. articulating defect site) | X | X | X |

Gross Morphological Observations: Following collection of the knee joints, the joints are opened, photographed and the surface of the defect site scored as indicated in Table 5. The synovial membrane was examined for inflammation. Joint fluid was collected and analyzed.

TABLE 5

Scoring Criteria for Gross Morphological Evaluations

| Characteristic | Grading | Score |
|---|---|---|
| Edge Integration (new tissue relative to native cartilage) | Full | 2 |
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or translucency of the neocartilage | Transparent | 2 |
| | Translucent | 1 |
| | Opaque | 0 |

Histology and Histological Evaluation: The knees were opened under sterile conditions and a culture swab obtained. Synovium was documented macroscopically and the defects are photographed and the joint grossly examined. The distal femur was removed and placed in 10% neutral buffered formalin for 12 hours. Areas of trochlea containing the defects and the harvest sites were dissected and placed into 10% formalin for 4 days. The specimens were subsequently placed into a decalcification solution (100 g Tritriplex (Epignost, Austria) and 33 g Tris-hydroxymethylene-amnomethane (Merck Eurolab, Belgium) per liter) for two to four days at room temperature. The decalcified specimens are embedded in paraffin and cut in a microtome to 5 µm thick sections.

Sections are stained with hematoxylin and eosin (H&E), safranin O/Fast Green, alcian blue and azan for evaluation of tissue types. Immunohistochemistry with antibodies for type I and type II collagens is performed according to a standard ABC protocol using HRP conjugated antibodies. Normal healthy ovine cartilage and tendon served as controls.

Light microscopy is performed on a Vanox Olympus research microscope implementing a histomorphometric method to determine the percentage of selected tissue types (analySiS). Multiple serial transverse histological sections from the middle portion of the defect are evaluated. The filling of the defect is determined as an area percentage of reparative tissue in the defect, based on the cross-sectional area in a sagittal plane through the center of the lesion. The area of the defect, of the filling, height and base of the defect, and tissue type are evaluated. The tissue types are characterized as follows: 1. fibrous tissue 2. transitional tissue 3. hyaline tissue and 4. articular cartilage. Semiquantitative analysis of the defect and adjacent tissue are done according standard scores adapted from O'Driscoll, Pineda and Frenkel.

Example 15

Human Clinical Trial

A feasibility study to evaluate the safety and performance of the fibrin matrices of the invention in the treatment of chronic cartilage defects of the femoral condyle has been submitted and approved (Ethics Committee of the Vienna University Hospital).

A phase I, non-randomized, open label, safety study using a fibrin matrix or a cell-bearing fibrin matrix prepared using plasminogen-free fibrinogen and autologous chondrocyte in patients is performed. Patients meeting the entrance criteria will undergo an arthroscopic procedure to confirm diagnosis and to harvest a biopsy for the growth of chondrocytes for future transplantation. Three to six weeks following cell harvest, patients will be hospitalized for surgery. After surgery, patients will be monitored for safety as follows: during 5-7 days hospitalization; after discharge at week 2 and week 6, and performance evaluation at week 12, month 6, and month 12.

The primary end is to evaluate the safety of a cell-bearing matrix of the invention, wherein the matrix serves as a scaffold for the seeding and transplantation of autologous chondrocytes in the treatment of a chronic cartilage condyle lesion.

The secondary endpoint is to evaluate the performance of a cell-bearing matrix in restoring function, as measured by an improvement in: MRI scores, Quality of life questionnaire, Joint function score. The safety parameters will include vital signs, serum chemistry, hematology and systemic and local adverse events. All parameters including patient inclusion and exclusion criteria and patient withdrawal criteria are presented.

Example 16:

One-Step Procedure for Treating Damaged Cartilage: Suitable For Arthroscopy or Hemi-Arthrotomy Autologous chondrocyte implantation has proven clinically effective in restoring hyaline-like cartilage to isolated chondral defects of the knee. The present therapies include three major steps:
1. Diagnostic Arthroscopy and biopsy of healthy cartilage.
2. Cultivation of cells.
3. Injection of cultured chondrocytes into the lesion under a periosteal flap, which is taken from the tibia and sutured over the lesion.

The disadvantages of the technique include the need for two separate surgical procedures, the requirement for a second site surgery to isolate a periosteal flap and the tendency for cartilage overgrowth due to the presence of the flap. An improved variation of this technique provides implant of the matrix of the present invention. A less traumatic method is presented herein, wherein the patient undergoes a single surgical procedure for cartilage repair.

Procedure: A patient with a cartilage defect may donate autologous plasma several days prior to the arthroscopy or hemi-arthrotomy. Blood (approximately 100-250 ml) is drawn and plasma proteins are purified, removing plasminogen. A plasma protein matrix, or several matrices, is prepared, labeled and stored aseptically until the day of the surgery.

Optionally, on the day of the surgery, cartilage from the patient's joint is removed, cut into small pieces and placed in a test tube containing collagenase, hyaluronidase or other cartilage degrading enzymes, or combinations thereof.

The surgeon treats the defective region of the joint by removing damaged tissue, cleansing and preparing the area for an implant. The prepared matrix is removed from its container and cut to fit the defective domain. Following approximately 20-30 minutes of enzymatic treatment, the cells and small pieces of cartilage are spun down in a tabletop centrifuge, rinsed in PBS and resuspended in a small amount (50 ul-1000 ul) of PBS. The surgeon seeds the cells onto the sponge, in situ. Alternatively, the cells are absorbed into the sponge and the cell-bearing sponge implanted into the defective joint region. Optionally, extracellular matrix degrading enzymes and or other bioactive agents including growth factors and/or anti-inflammatory compounds are added to the sponge. In certain instances the surgeon will place a dry sponge directly onto the injured area, optionally add enzyme solution to said sponge and place a second, cell-bearing sponge on top of the first sponge. The joint is closed and is treated as customary for an arthroscopic or hemi-arthrotomy procedure and the patient is released to recover.

Kit

A kit comprising the components useful for practicing the method of the invention, will allow for the convenient practice of the method of the invention in a surgical setting. In one embodiment, a kit of the invention will provide sterile components suitable for easy use in the surgical environment including, sterile solutions (saline, enzymes) a sterile, cell-free matrix material suitable for supporting autologous chondrocytes that are to be implanted into an articular joint surface defect and instructions for use.

Example 17

Bone Repair Model

The plasma protein matrix of the present invention is useful for the treatment of bone defects including osteotomy, particularly in non-weight bearing regions of the skeleton. Suitable animal models are used to create bilateral osteotomies to demonstrate the efficacy of the present invention. In an exemplary rabbit model a 4-6 mm osteotomy is created in New Zealand Rabbits in compliance with the Animal Care Committee. The ulna is chosen because it is only slightly weight-bearing and allows the creation of a bone defect without requiring a cast or other immobilization treatment. In addition, this gap constitutes a spontaneously healing defect that allows the evaluation of the tested agent. The primary indices of fracture healing are accelerated duration of healing and callus formation. The test compounds consist of matrices of the invention and control matrices.

Surgery procedure: Animals are anesthetized according to standard protocol. Gap formation is performed in the mid ulna bone. A sponge of the invention is placed into the gap area in each limb and the fracture is closed. Animals are treated with analgesic for 3 days post operation. The duration of the experiment is 6 weeks.

Healing time and quality assessment: X-ray grading provides fracture healing status assessment. Rabbits are X-rayed every other week for 5 weeks after surgery. X-rays are scored by two orthopedic surgeons in a blinded manner according to a standard grading scale protocol.

Quality evaluation: at the end of the experiment, rabbits are sacrificed and fracture area is sent for histological and mechanical strength evaluation. Histology is scored by a pathologist for evaluation of histological changes during the healing process using standard staining methods, using hematoxylin and eosin (H&E) for cytoplasm and nucleus. Indigo-carmin staining is also applied for detection of newly generated callus. Mechanical strength evaluation is performed using the "4 points bending" method.

The treatments groups are: sham osteotomy, osteotomy treated with fibrin sponge alone, osteotomy treated with fibrin sponge comprising glycosaminoglycan, osteotomy treated with a fibrin sponge comprising glycosaminoglycan, optional heparin growth factors.

Another example of an animal model for bone repair is presented in Cook et al., (Am J. Vet Res 64:2-20, 2003).

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A porous freeze-dried fibrin matrix formed from plasma proteins comprising fibrinogen cleaved by the action of thrombin at varying concentrations sufficient to cleave said fibrinogen and Factor XIII, the matrix having less than 10% residual moisture and being devoid of exogenous anti-fibrinolytic agents and of organic chelating agents, wherein the plasma proteins comprise partially purified plasma proteins that are devoid of plasminogen.

2. The porous freeze-dried fibrin matrix according to claim 1, wherein the plasma proteins comprise less than about 5% of plasminogen normally present in plasma.

3. The porous freeze-dried fibrin matrix according to claim 2, further comprising at least one additive, wherein said at least one additive is a glycosaminoglycan and at least one bioactive agent, wherein said at least one bioactive agent is a growth factor.

4. The porous freeze-dried fibrin matrix according to claim 3, wherein said glycosaminoglycan is a crosslinked or non-crosslinked hyaluronic acid.

5. The porous freeze-dried fibrin matrix according to claim 3, wherein said growth factor is a fibroblast growth factor.

6. The porous freeze-dried fibrin matrix according to claim 5, wherein said fibroblast growth factor is selected from the group consisting of FGF2, FGF4, FGF9, and FGF18.

7. The porous freeze-dried fibrin matrix according to claim 6, further comprising cells.

8. The porous freeze-dried fibrin matrix according to claim 7, wherein the cells that are present are selected from the group consisting of stem cells, progenitor cells, chondrocytes, osteoblasts, hepatocytes, and mesenchymal, endothelial, epithelial, urothelial, endocrine, neuronal, pancreatic, renal and ocular cell types.

9. The porous freeze-dried fibrin matrix according to claim 1, wherein at least one of the plasma proteins is autologous or at least one of the plasma proteins is recombinant.

10. A porous freeze-dried fibrin matrix formed from plasma proteins comprising fibrinogen cleaved by the action of thrombin at varying concentrations sufficient to cleave said fibrinogen and Factor XIII, the matrix having less than 10% residual moisture and being devoid of exogenous anti-fibrinolytic agents, plasminogen and of organic chelating agents.

11. The porous freeze-dried fibrin matrix according to claim 10, wherein the plasma proteins comprise less than 20% of the plasminogen normally present in plasma.

12. The porous freeze-dried fibrin matrix according to claim 11, further comprising at least one additive, wherein said at least one additive is a glycosaminoglycan and at least one bioactive agent, wherein said at least one bioactive agent is a growth factor.

13. The porous freeze-dried fibrin matrix according to claim 12, wherein said glycosaminoglycan is a crosslinked or non-crosslinked hyaluronic acid.

14. The porous freeze-dried fibrin matrix according to claim 12, wherein said growth factor is a fibroblast growth factor selected from the group consisting of FGF2, FGF4, FGF9, and FGF18.

15. The porous freeze-dried fibrin matrix according to claim 14, further comprising cells selected from the group consisting of stem cells, progenitor cells, chondrocytes, osteoblasts, hepatocytes, and mesenchymal, endothelial, epithelial, urothelial, endocrine, neuronal, pancreatic, renal and ocular cell types.

16. The porous freeze-dried fibrin matrix according to claim 12, wherein at least one of the plasma proteins is autologous.

* * * * *